(12) United States Patent
Corbett et al.

(10) Patent No.: US 6,384,220 B2
(45) Date of Patent: May 7, 2002

(54) PARA-ARYL OR HETEROCYCLIC SUBSTITUTED PHENYL GLUCOKINASE ACTIVATORS

(75) Inventors: Wendy Lea Corbett, Randolph; Nancy-Ellen Haynes, Cranford; Ramakanth Sarabu, Cedar Grove, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/846,821

(22) Filed: May 1, 2001

Related U.S. Application Data
(60) Provisional application No. 60/202,387, filed on May 8, 2000.

(51) Int. Cl.[7] ............... C07D 265/30; C07D 277/44; C07C 271/00
(52) U.S. Cl. ............ 544/168; 546/337; 548/205; 548/338.5; 548/494; 560/24; 560/38; 562/443; 564/155
(58) Field of Search .............. 544/168; 546/337; 548/205, 338.5, 494; 560/24.38; 562/443; 564/155

(56) References Cited

U.S. PATENT DOCUMENTS

| | | | |
|---|---|---|---|
| 3,776,917 A | | 12/1973 | Mann et al. |
| 5,288,733 A | * | 2/1994 | Raddatz et al. ............. 514/311 |
| 5,693,650 A | * | 12/1997 | Muller et al. ............... 514/311 |

FOREIGN PATENT DOCUMENTS

| | | |
|---|---|---|
| WO | WO 00/58293 | 10/2000 |

OTHER PUBLICATIONS

Colowick, S.P., *The Enzymes, vol. IX, Part B*, pp. 1–48 (1973), Academic Press, NY.
Chipkin et al., *Joslin's Diabetes Mellitus*, 13th Edition, pp. 97–1165 (1994).
Olson, R. E. et al., *Annual Review of Nutrition, vol.* 13 pp. 463–496 (1993).
Meglasson, M..D., et al., *Amer. J. Physiol. vol.* 246. E1–E13 (1984).
Grupe, A. et al., *Cell, vol.* 83, pp. 69–78 (Oct.1995).
Ferie, T. et al., *FASEB Journal, vol.* 10, pp. 1213–1218 (1996).
Liang, Y., *Biochem Journal, vol.* 305, pp. 167–173 (1995).
Glaser, B., et al. *Neew England Journal of Medicine, vol.* 338, pp. 226–230 (1998).

* cited by examiner

*Primary Examiner*—Zinna Northington Davis
(74) *Attorney, Agent, or Firm*—George W. Johnston; Patricia S. Rocha-Tramaloni; Arthur D. Dawson

(57) ABSTRACT

Para-aryl or heteroaryl substituted phenyl amides which are active as glucokinase activators to increase insulin secretion which makes them useful for treating type II diabetes.

95 Claims, No Drawings

PARA-ARYL OR HETEROCYCLIC SUBSTITUTED PHENYL GLUCOKINASE ACTIVATORS

PRIORITY TO PROVISIONAL APPLICATION UNDER 35 U.S.C. § 119(e)

This application claims priority under 35 U.S.C. §119(e) of provisional application Serial No. 60/202,387, filed on May 8, 2000.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides a compound, comprising an amide of the formula:

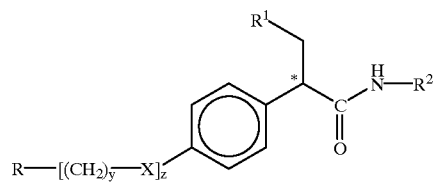

I wherein X is —O— or

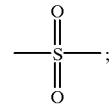

R is a heteroaromatic ring, connected by a ring carbon atom, which contains from 5 to 6 ring members with from 1 to 3 heteroatoms selected from the group consisting of oxygen, sulfur or nitrogen, aryl containing 6 or 10 ring carbon atoms, aryl fused with a heteroaromatic ring which contains from 5 to 6 ring members with 1 to 3 heteroatoms in the ring being selected from the group consisting of nitrogen, oxygen or sulfur, a saturated 5- or 6-membered cycloheteroalkyl ring which contains from 1 to 2 heteroatoms selected from the group consisting of oxygen, sulfur and nitrogen, or a cycloalkyl ring having 5 or 6 carbon atoms; $R^1$ is a cycloalkyl ring having from 5 or 6 carbon atoms; $R^2$ is

a five- or six-membered heteroaromatic ring connected by a ring carbon atom to the amide group shown, which contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted at a position on a ring carbon atom other than adjacent to said connecting carbon atom with a substituent selected from the group consisting of lower alkyl,

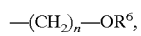

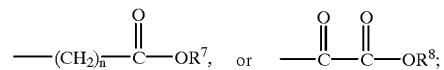

n is 0, 1, 2, 3 or 4; y and z are independently 0 or 1; $R^3$ is hydrogen, lower alkyl or

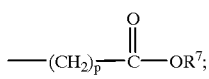

$R^6$, $R^7$ and $R^8$ are independently hydrogen or lower alkyl; p is an integer from 0 to 5; and * denotes the asymmetric carbon atom center; or a pharmaceutically acceptable salt thereof.

The compounds of formula I are glucokinase activators are useful for increasing insulin secretion in the treatment of type II diabetes.

DETAILED DESCRIPTION OF THE INVENTION

The compounds of formula I have the following embodiments

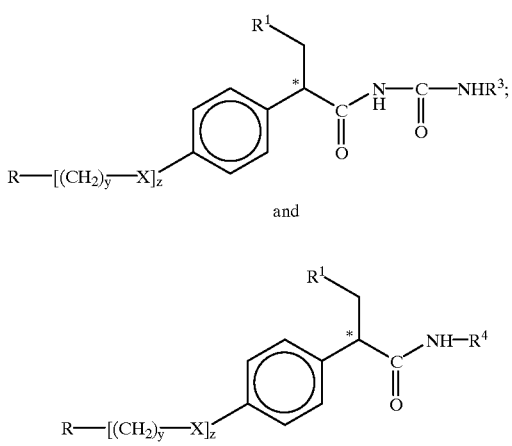

wherein

R, $R^1$, $R^3$, X, y, n and z are as above;

$R^4$ is a five- or six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted at a position on a ring carbon atom other than adjacent to said connecting carbon atom with a substituent selected from the group consisting of lower alkyl,

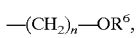

—$(CH_2)_n$—$OR^6$,

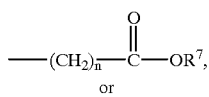

or

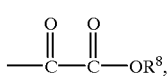

n is 0, 1, 2, 3 or 4;

$R^6$, $R^7$ and $R^8$ are independently hydrogen or lower alkyl; or a pharmaceutically acceptable salt thereof.

In the compound of formulae I, IA and IB, the "*" designates the asymmetric carbon atom in this compound with the R optical configuration being preferred. The compounds of formula I may be present in the pure R form or as a racemic or other mixtures of compounds having the R and S optical configuration at the asymmetric carbon shown. The pure R enantiomers are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, the term "halogen or halo" unless otherwise stated, designates all four halogens, i.e. fluorine, chlorine, bromine and iodine.

R can be any five- or six-membered saturated cyclic heteroalkyl ring containing from 1 to 2 heteroatoms selected from the group consisting of sulfur, oxygen or nitrogen. Any such five- or six-membered saturated heterocyclic ring can be used in accordance with this invention. Among the preferred rings are morpholinyl, pyrrolidinyl, piperazinyl, piperidinyl, etc.

As used herein, the term "aryl" signifies "polynuclear" and mononuclear unsubstituted aromatic hydrocarbon groups such as phenyl or naphthyl containing either 6 or 10 carbon atoms.

The heteroaromatic ring defined by R, $R^2$ and $R^4$ can be five- or six-membered heteroaromatic ring having from 1 to 3 heteroatoms selected from the group consisting of oxygen, nitrogen, and sulfur which is connected by a ring carbon to the remainder of the molecule as shown. The heteroaromatic ring defined by $R^2$ and $R^4$ contains a first nitrogen heteroatom adjacent to the connecting ring carbon atom and if present, the other heteroatoms can be oxygen, sulfur, or nitrogen. Among the preferred heteroaromatic rings include pyridinyl, pyrimidinyl and thiazolyl. On the other hand, the heteroaromatic ring defined by R need not contain a nitrogen heteroatom. These heteroaromatic rings which constitute $R^2$ or $R^4$ are connected via a ring carbon atom to the amide group to form the amides of formula I. The ring carbon atom of the heteroaromatic ring which is connected via the amide linkage to form the compound of formula I does not contain any substituent. When $R^2$ or $R^4$ is an unsubstituted or mono-substituted five- or six-membered heteroaromatic ring, the rings contain a nitrogen heteroatom adjacent to the connecting ring carbon.

When R is aryl fused with a heteroaromatic ring, the term "aryl" is as defined above and the term "heteroaromatic" is as defined above. In the compounds of formulae I, IA and IB, the preferred aryl is phenyl. The heteroaromatic substituent is connected to the remainder of the molecule through the aryl substituent. The preferred heteroaromatic ring formed by fusing to aryl substituents which define R, are indolyl, quinolyl, isoquinolyl, 2H-chromanyl and benzo[b]thienyl. When R is a cycloalkyl group, R can be any cycloalkyl group containing 5 or 6 carbon atoms such as cyclohexyl or cyclopentyl.

The term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2.0 to 3. Particularly preferred amino protecting groups such as t-butoxycarbonyl carbamate, benzyloxycarbonyl carbamate, 9-flurorenylmethyl carbamate.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

During the course of the reaction the various functional groups such as the free carboxylic acid or hydroxy groups will be protected via conventional hydrolyzable ester or ether protecting groups. As used herein the term "hydrolyzable ester or ether protecting groups" designates any ester or ether conventionally used for protecting carboxylic acids or alcohols which can be hydrolyzed to yield the respective hydroxyl or carboxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

The compounds of formula I-B have the following embodiments:

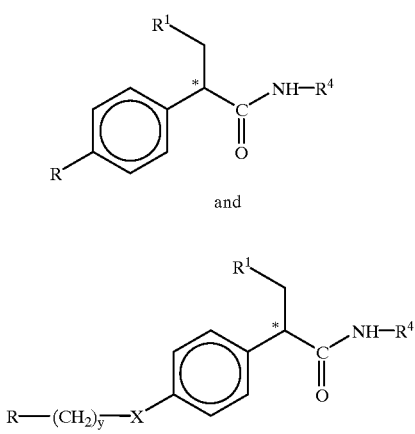

wherein

X, R, $R^1$, $R^4$, * and y are as above.

Among the compounds of formulae IB-1 and IB-2 are those compounds where $R^1$ is cyclopentyl, i.e., the compounds of formulae I-B1(a) and I-B2(a). Among the embodiments of compounds of formula I-B1(a) are those compounds where R is aryl [the compound of formula I-B1(a)(1)]. Among those compounds of formula I-B1(a)(1) are those compounds where $R^4$ is an unsubstituted thiazolyl;

thiazolyl substituted with

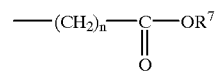

wherein n and $R^7$ are as above;

thiazolyl substituted with $-(CH_2)_n-OR^6$ or

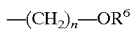

where n, R, $R^6$ and $R^8$ are as above;
an unsubstituted pyridinyl;
pyridinyl monosubstituted with

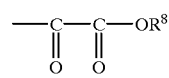

where n and $R^7$ are as above; or
pyridinyl monosubstituted with $-(CH_2)_n-OR^6$ where $R^6$ and n are as above.

Among the embodiments of compounds of formula I-B1(a) are those compounds where R is a heteroaromatic ring containing from 5 to 6 ring members with from 1 to 2 heteroatoms selected from the group consisting of oxygen, nitrogen and sulfur. In this case, the preferred embodiments are those compounds where $R^4$ is an unsubstituted pyridinyl or thiazolyl. In accordance with this preferred embodiment, where $R^4$ is pyridinyl or thiazolyl, the heteroaromatic substituent defined by R is, most preferably, also pyridinyl or thiophenyl.

Other embodiments of the compounds of formula I-B1(a) are those compounds where R is aryl fused to a 5- or 6-membered heteroaromatic ring containing from 1 to 2 heteroatoms in the ring selected from the group consisting of oxygen, sulfur and nitrogen. In this case, the preferred embodiment are those compounds where $R^4$ is thiazolyl. Among the embodiments of compounds of formula I-B2(a) are those compounds where X is —O— [the compound of formula I-B2(a)(1)]. Among the embodiments of the formula of I-B2(a)(1) are compounds where R is aryl. In this case, the preferred compounds are those where $R^4$ is unsubstituted or substituted pyridinyl or thiazolyl.

Among the embodiments of the compounds of formula I-B2(a) are those compounds where X is

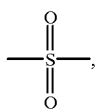

the compounds of formula I-B2(a)(2). Among the embodiments of the compounds of formula I-B2(a)(2) are those compounds where R is aryl, with compounds where $R^4$ is thiazolyl being especially preferred. Among the embodiments of the compounds of formula I-B(2)a(2) are those compounds where R is cycloalkyl and $R^4$ is thiazolyl.

Among the embodiments of the compounds of formula I-B2(a)(2) are those compounds where R is a heteroaromatic ring and preferably, in this case those compounds where $R^4$ is thiazolyl.

The compounds of formula I-A have the following embodiments:

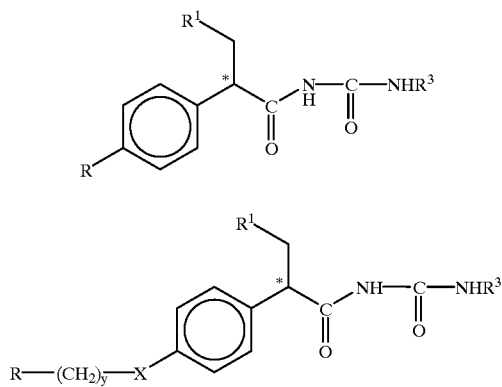

where

X, R, $R^1$, $R^3$ and y are as above.

Among the embodiments of compounds of the formulae I-A1 and I-A2 are those compounds where $R^1$ is cyclopentyl, i.e., the compounds of formulae I-A1(a) and I-A2(a). Among the embodiments of the compounds of formulae I-A1(a) and I-A2(a) are those compounds where R is aryl;

R is a 5- or 6-membered heteroaromatic ring containing from 1 to 3 heteroatoms selected from the group consisting of oxygen, nitrogen and sulfur;

R is a saturated 5- or 6-membered cycloheteroalkyl ring containing from 1 to 2 heteroatoms selected from the group consisting of oxygen, nitrogen and sulfur; and R is cycloalkyl.

The compounds of formulae I-B1 and I-A1 can be prepared from compounds of the formula

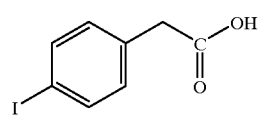

The compounds of formulae IB-1 and IA-1 are produced from the compound of formula V via the following reaction scheme:

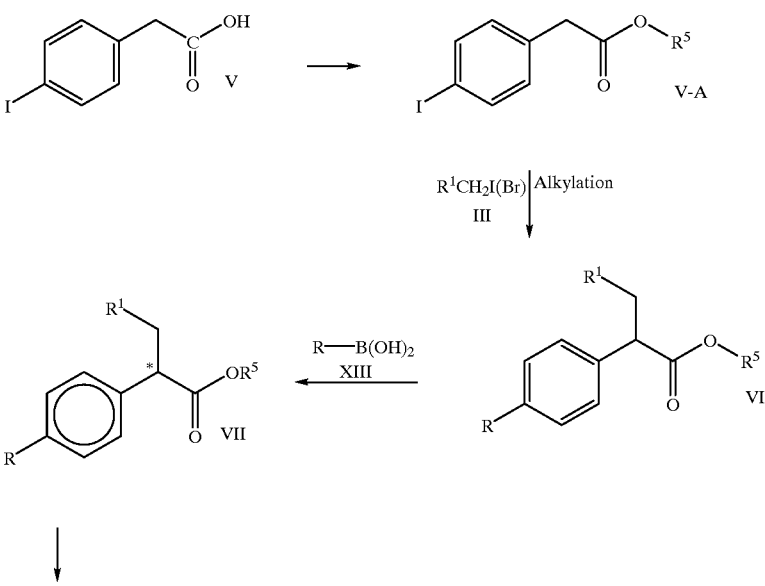

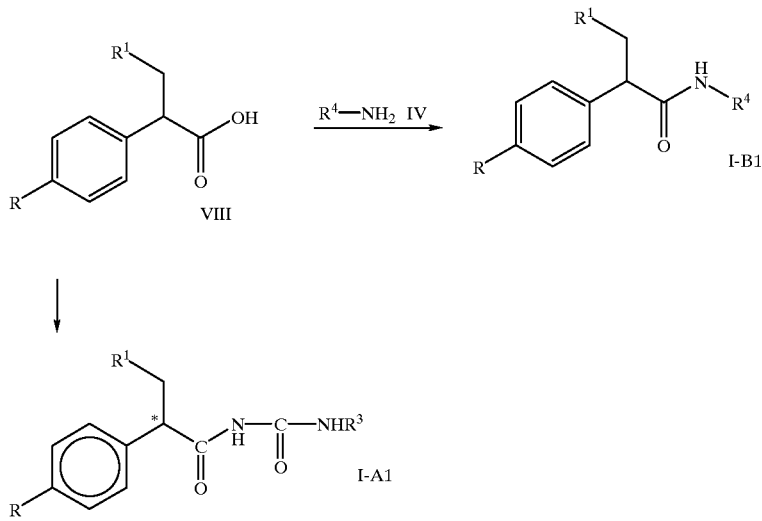

wherein
R, $R^1$, $R^3$ and $R^4$ are as above and $R^5$, taken together with its attached oxygen atom forms a hydrolyzable ester.

In the first step of this reaction, the carboxylic acid group of the compound of formula V is protected by converting it to a hydrolyzable ester protecting group. In this conversion, the compound of formula V is converted to the compound of formula V-A treating the compound of formula V with an organic alcohol such as a lower alkanol in the presence of a strong inorganic acid such as sulfuric acid. In carrying out this reaction, any conventional method of esterification can be utilized. In accordance with the preferred embodiment, the ester of formula V-A is a methyl ester produced by reacting the compound of formula V with methanol utilizing sulfuric acid as an esterification catalyst. In the next step, the compound of formula V-A is alkylated with the compound of formula III to produce the compound of formula VI. Any conventional method of alkylating the alpha carbon atom of an organic acid ester with an alkyl bromide or iodide can be utilized to effect this conversion and produce the compound of formula VI. In the next step of this reaction, the compound of formula VI is coupled with the compound of formula XIII to produce the compound of formula VII via a Suzuki coupling reaction. These coupling reactions are carried out in an inert organic polar solvent, preferably dimethylformamide and dimethoxyethane utilizing a tertiary amine such as tri-lower alkyl amine, preferably tri-ethylamine and a ligand forming reagent. Among the preferred ligand forming reagents are tri-lower alkyl or tri-aryl phosphines. This reaction is carried out in the presence of a noble metal catalyst such as a palladium II catalysts, preferably palladium diacetate. In carrying out this reaction, temperatures of from 80° C. to the reflux temperature of a solvent medium are utilized. In the next step, the compound of formula VII is converted to the compound of formula VIII by hydrolyzing the $R^5$ protecting group to form the corresponding organic acid of formula VIII. Any conventional method of hydrolyzing an ester can be utilized to effect this conversion. In the next step of this process, the organic acid of formula VIII is reacted with the amine of formula IV to produce the compound of formula I-B1. This reaction is carried out by condensing the compound of formula IV with the compound of formula VIII to form the amide of formula I-B1. This condensation reaction can be carried out utilizing any of the conventional means for amide formation.

On the other hand, the compound of formula VIII can be converted to the compound of formula IA-1. The coupling of the compound of formula VIII with either compounds of the formulae

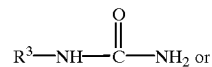

XII-A wherein $R^3$ is as above produces the compound of formula IA-1.

The carboxylic acid of formula VIII can be converted to the corresponding amide. This amide formation is carried out in two steps first by converting the carboxylic acid of formula VIII to the corresponding acid chloride and then by reacting this acid chloride with ammonia. Any of the conditions conventional for converting a carboxylic acid to a corresponding carboxylic acid chloride can be utilized in this procedure. Furthermore the reactions of carboxylic acid chloride with ammonia to produce the corresponding amide is also a well known reaction and the conditions conventional in this well known reaction can be utilized in the formation of the amide corresponding to the compound of formula VIII. The amide is then reacted with the isocyanate of formula XII-B to form the urea adduct of the compound of formula I-A1. Any conventional method of reacting an isocyanate with an amide to form a urea linkage can be utilized to produce the compound of formula I-A1. On the other hand, the acid chloride can directly reacted with the compound of urea reagent formula X11-A to produce a urea adduct. Any of the conditions conventional in a method of reacting a chloride with a urea reagent can be utilized in carrying out this procedure.

The compound of formula V-A wherein R is cycloalkyl or aryl are known compounds. On the other hand, compounds of formula V-A wherein R is a heteroaromatic ring or a saturated 5 to 6-membered heteroalkyl ring or aryl fused with a heteroaromatic ring can be prepared from known compounds of formula:

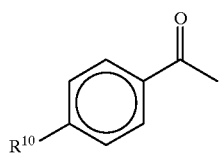

wherein $R^{10}$ is a heteroaromatic ring containing from 5 to 6 ring members with from 1 to 2 heteroatoms selected from the group consisting of oxygen, sulfur and nitrogen; a saturated 5- or 6-membered cycloheteroalkyl ring containing from 1 to 2 heteroatoms selected from the group consisting of oxygen, sulfur and nitrogen; or aryl fused with a heteroaromatic ring which contain 5 or 6 ring members with 1 to 3 heteroatoms in the ring being selected from the group consisting of nitrogen, oxygen and sulfur.

The compound of formula XI is converted to the compound of formula VIII, where R is $R^{10}$ (the compound of formula VIII-A), by the following reaction scheme:

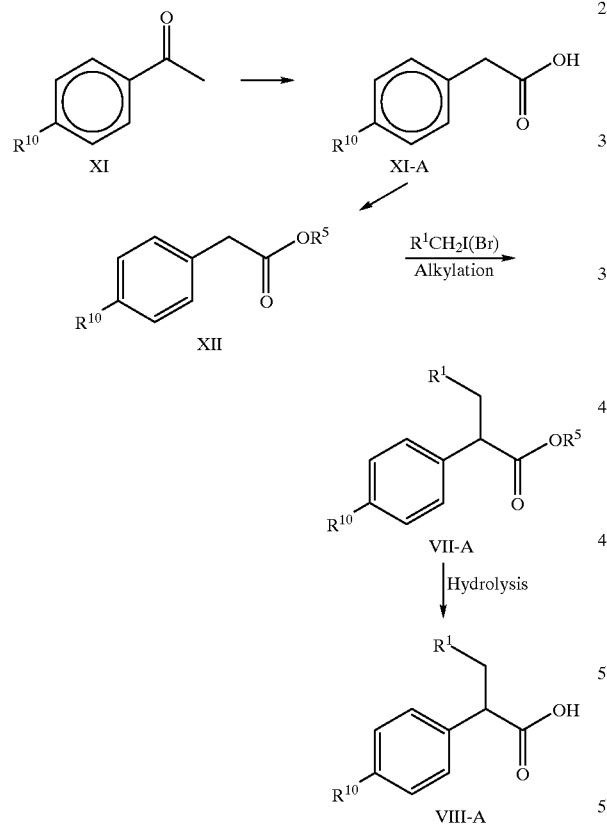

wherein $R^1$, $R^5$ and $R^{10}$ are as above.

The compound of formula XI is converted to the compound of formula XI-A by utilizing any conventional means of converting an acetophenone to acetic acid. In general, this reaction is carried out by treating the compound of formula XI with morpholine in a inert organic solvent while heating to a temperature of above 80° C. to reflux. While this is done, acetic acid and sulfuric acid are added to the reaction mixture to cause the methyl ketone to convert to acetic acid derivative of formula XI-A. The compound of formula XI-A is esterified with a conventional esterifying agent so that the free acid forms a hydrolyzable ester of formula XII. This reaction is carried out utilizing the same procedure described in connection with the conversion of the compound of formula V to the compound of formula V-A. The compound of formula XII is then alkylated with the compound of formula III to produce the compound of formula VII-A. This reaction is carried out in the same manner as disclosed in connection with the conversion of the compound of formula V-A to the compound of formula VI. The compound of formula VII-A is then hydrolyzed as described hereinbefore in connection with the conversion of the compound of formula VII to the compound formula VIII to produce to the compound of formula VIII-A. The compound of formula VIII-A can be converted to the compounds of formulae I-A1 and I-B1, where R is $R^{10}$, in the manner described herein before in connection with the conversion of the compound of formula VIII to the compounds of formulae I-A1 and I-B1.

When in the compound of formula I, when X is —O—, y is 0 and z is 1, i.e., compounds of the formula

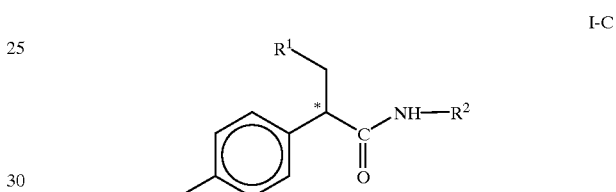

wherein

R, $R^1$ and $R^2$ are as above, these compounds are prepared from compounds of the formula

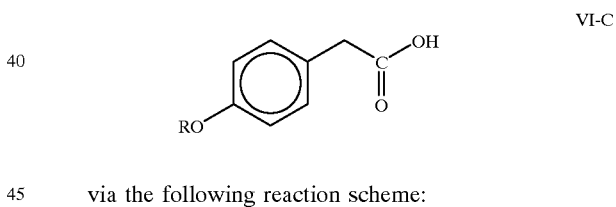

via the following reaction scheme:

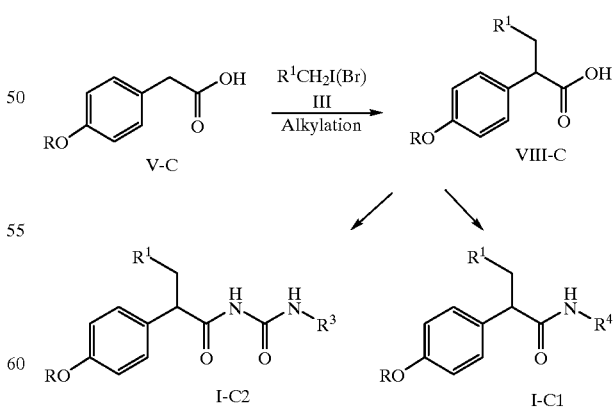

wherein

R, $R^1$, $R^3$ and $R^4$ are as above.

The compound of the formula V-C is converted to the compound of formula VIII-C by alkylation with the compound of formula III in the same manner described in connection with the conversion of the compound of formula V-A to the compound of formula VI. The compound of formula VIII-C can be converted to the compound of formula I-C1 in the same manner as described for the conversion of the compound of formula VIII to the compound of formula I-B1. On the other hand, the compound of formula VIII-C can be converted to the compound of formula I-C2 in the same manner as described in connection with the conversion of compound of formula VIII into the compound of formula I-A1.

On the other hand, when X is O and y is 1, the compound of formula:

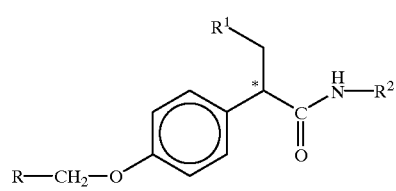

I-D wherein

R, $R^1$ and $R^2$ are as above.

These compounds can be prepared from compounds of the formula

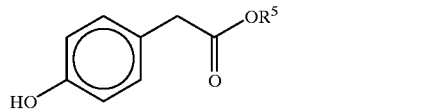

wherein $R^5$ is as above, via the following reaction scheme:

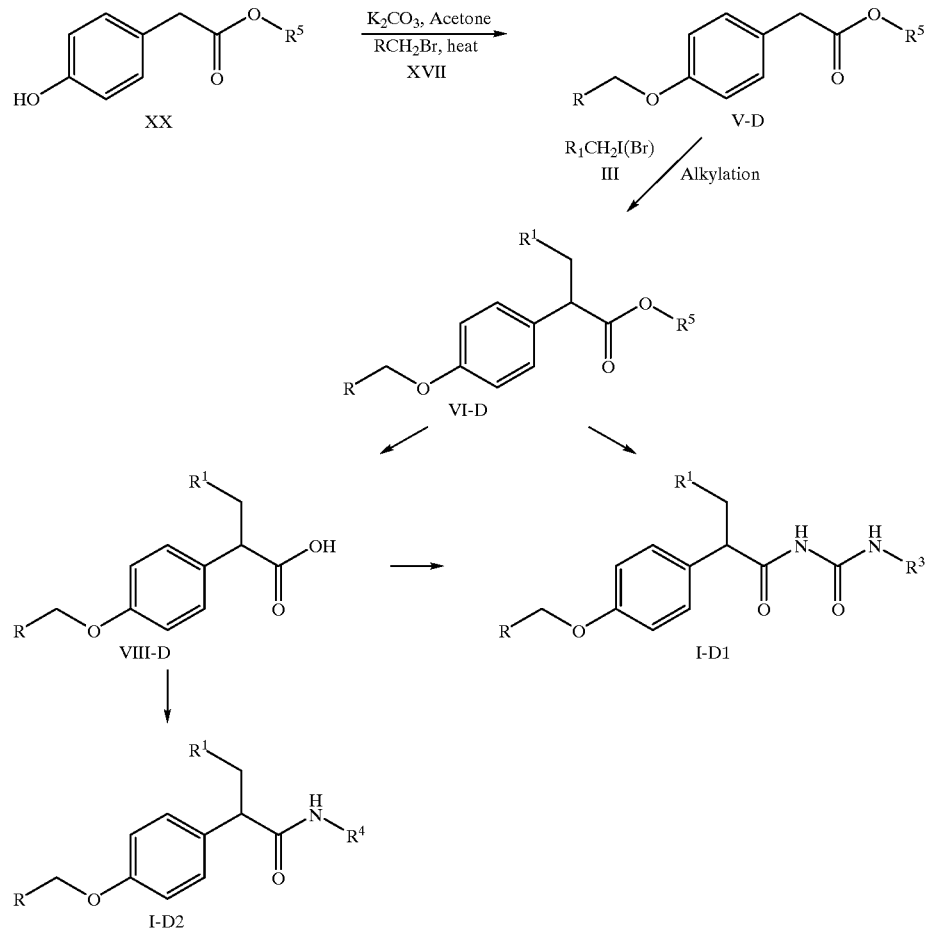

The compound of formula XX is condensed with the compound of formula XVII to produce the compound of formula V-D utilizing any of the known procedures for condensing an alcohol with an alkyl bromide to form an ether. Any of the conditions conventionally utilized in forming an ether by utilizing a bromide and an alcohol can be utilized to affect this conversion. In accordance with the preferred embodiment of this invention, this reaction is carried out in the presence of an alkaline earth metal carbonate in the presence of an organic solvent such as acetone. In carrying out this reaction, elevated temperatures are utilized, i.e., temperatures of from about 80° C. to reflux.

The compound of formula V-D is converted to the compound of formula VI-D utilizing the same procedure described in connection with the reaction of the compound of formula III with the compound of formula V-A to produce the compound of formula VI. The compound of formula VI-D is converted to the compound of formula VIII-D by conventional hydrolysis as described hereinbefore. The compound of formula VIII-D can be converted to the compound of formula I-D2 in the same manner as described herein in connection with the conversion of formula VIII to the compound of formula I-B1. On the other hand, the compound of formula VIII-D can be converted to the compound of formula I-D1 utilizing the same procedure as described hereinbefore in converting the compound of formula VIII to the compound of formula I-A1.

In accordance with another embodiment of this invention, the compound of formula I wherein y is 0 or 1 and X is

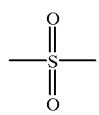

i.e., a compound of the formula

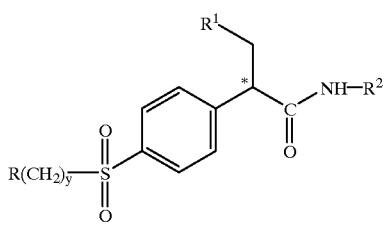

wherein y, R, $R^1$ and $R^2$ are as above, can be prepared from a compound of the formula

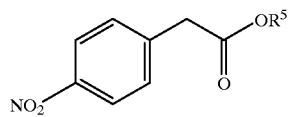

XXIX wherein $R^5$ is as above, via the following reaction scheme:

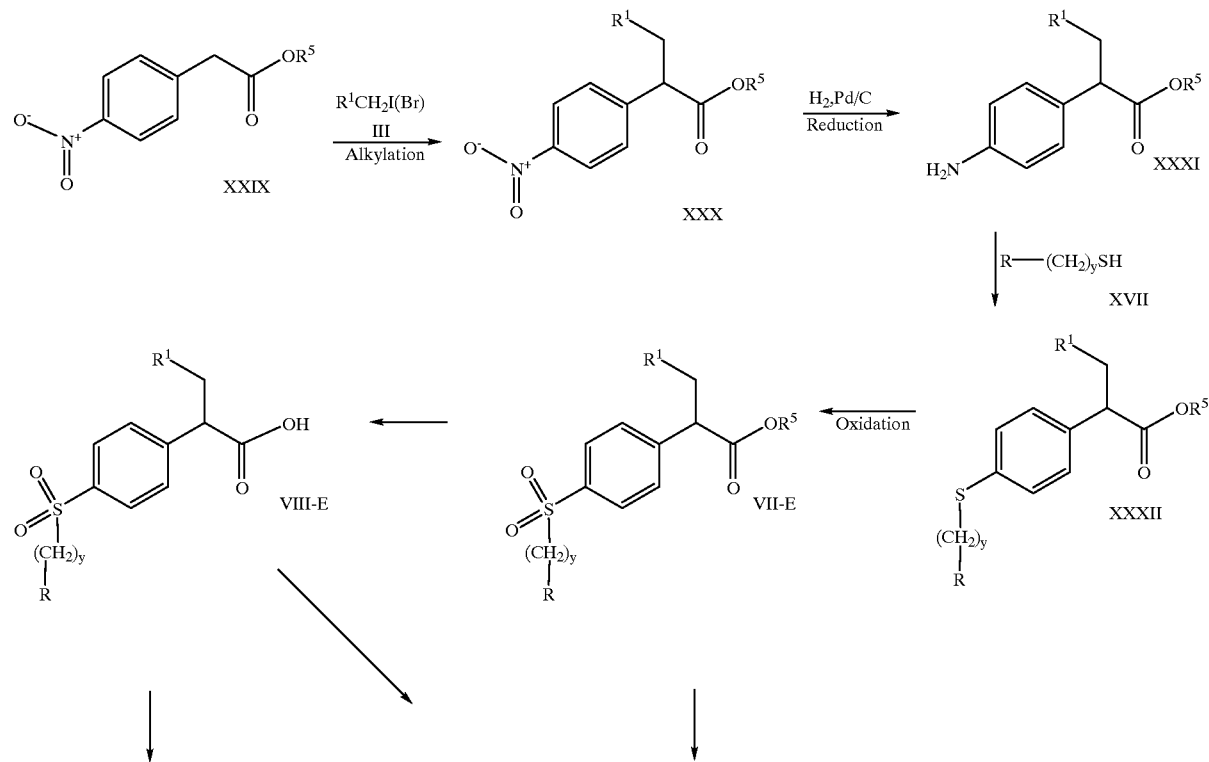

-continued

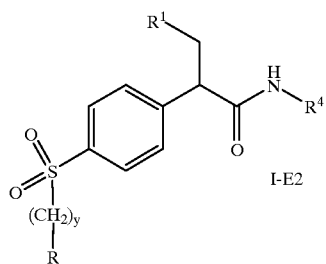

I-E2

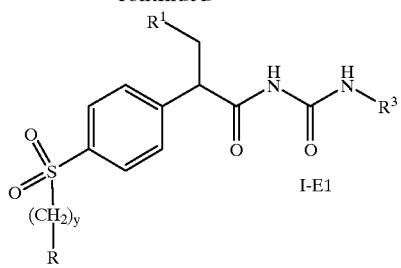

I-E1

In this procedure, the compound of formula XXIX is reacted with the compound of formula III via an alkylation reaction to produce the compound of formula XXX. This alkylation reaction is carried out in the same manner described in connection with the alkylation compound of formula V-A to the compound of formula VI by the reaction of the compound of formula VI-A with the compound of formula III. The compound of formula XXX is converted to the compound of formula XXXI by conventional reduction of a nitro group to an amine group. Any of the conditions conventional in reducing a nitro group to an amine group can be utilized. Among the preferred methods are hydrogenation over palladium carbon catalyst. The step of converting the compound of formula XXX to the compound of formula XXXI is carried out through the use of such conventional reduction techniques. In the next step of this reaction of compound of formula XXXI is converted the compound of formula XXXII by reacting the compound of formula XXXI with the compound of formula XVII. This is carried out by conventional means such as converting a phenylamino group to a phenylthio group by elimination of the amino substituent and the addition of the thio substituent to the phenyl ring. In the next step of the process, the compound of formula XXXII is converted to the compound of formula VII-E by oxidizing the thio group to a sulfone group. Any conventional method of oxidizing a thio to a sulfone group can be utilized in carrying out this procedure. The compound of formula VII-E is converted to the compound of formula VIII-E by conventional ester hydrolysis. The compound of formula VIII-E is converted to the compound of formula I-E I in accordance with the procedure already described in connection with the conversion of a compound of formula VIII to a compound of formula I-A1. On the other hand, the compound of formula VIII-E can be converted to the compound of formula I-E2 by the same procedure hereinbefore described in connection with the conversion of the compound of formula VIII to a compound of formula I-B1.

Those phenyl compounds of the formula

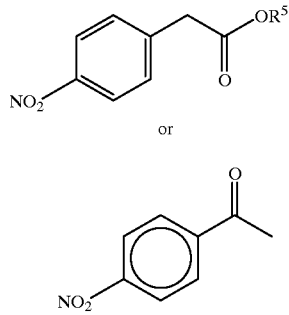

or are known compounds. When one wants to prepare the corresponding para iodo substituted phenyl compounds, these para iodo substituted phenyl compounds are formed from these known para nitro phenyl compounds listed above. The para nitro group can then be reduced to an amino group. Any conventional method of reducing a nitro group to an amine can be utilized to effect this conversion. This amine group can be used to prepare the corresponding para iodo compound via a diazotization reaction. Any conventional method of converting amino group to an iodo group (see, for example, Lucas, H. J.; Kennedy, E. R. *Org. Synth. Coll. Vol.*, II 11943, 351) can be utilized to effect this conversion.

The compound of formula I, "*" designates an asymmetric carbon atom through which the group —$CH_2R^2$ and the acid amide substituents are connected. In accordance with this invention, the preferred stereoconfiguration of this group is R.

If it is desired to produce the "R" or the S isomer of the compound of formula I, this compound can be separated into these isomers by any conventional chemical means. Among the preferred chemical means is to react the free acid compounds of formulae VIII, VIII-A, VIII-C, VIII-D or VIII-E with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula VIII is reacted with the optically active base in an inert organic solvent medium to produce salts of the optically active amine with both the R and S isomers of this compound of formula VIII. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula VIII in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula VIII which are produced by this method of resolution is carried out throughout the entire reaction scheme to produce the desired R or S isomer of formula I. The separation of R and S isomers can also be achieved using an enzymatic ester hydrolysis of any lower alkyl esters corresponding to the compound of the formula VIII (see for example, Ahmar, M.; Girard, C.; Bloch, R, *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula VIII is via the formation of corresponding diastereomeric esters or amides. These diastereomeric esters or amides can be prepared by coupling the carboxylic acids of the formula VIII with a chiral alcohol, or a chiral amine. This reaction can be carried out using any conventional method of coupling a carboxylic acid with an alcohol or an amine. The corresponding diastereomers of compounds of the formula VIII can then be separated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization.

All of the compounds of formula I which include the compounds set forth in the Examples, activated glucokinase in vitro by the procedure of Example A. In this manner, they increase the flux of glucose metabolism which causes increased insulin secretion. Therefore, the compounds of formula I are glucokinase activators useful for increasing insulin secretion.

EXAMPLE 1

2-Biphenyl-4-yl-3-cyclopentyl-N-thiazol-2-yl-propionamide

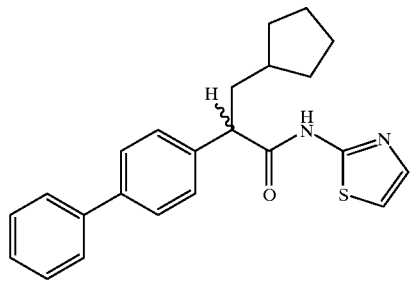

A solution of diisopropylamine (6.93 mL, 49.5 mmol) in dry tetrahydrofuran (64 mL) and 1,3-dimethyl-3,4,5,6-tetrahydro-2(1H)-pyrimidinone (16 mL) was cooled to −78° C. under nitrogen and then treated with a 2.5M solution of n-butyllithium in hexanes (19.8 mL, 49.5 mmol). The yellow reaction mixture was stirred at −78° C. for 30 min and then treated dropwise with a solution of 4-biphenylacetic acid (5.00 g, 23.6 mmol) in a small amount of dry tetrahydrofuran. The reaction mixture turned dark in color and was allowed to stir at −78° C. for 45 min, at which time, a solution of iodomethylcyclopentane (4.96 g, 23.6 mmol) in a small amount of dry tetrahydrofuran was added dropwise. The reaction mixture was allowed to warm to 25° C. over a period of 15 h. The reaction mixture was quenched with water (100 mL), and the reaction mixture was concentrated in vacuo to remove tetrahydrofuran. The remaining aqueous layer was acidified to pH=2 with concentrated hydrochloric acid and then extracted with ethyl acetate (2×150 mL). The combined organic extracts were dried over magnesium sulfate, filtered, and concentrated in vacuo. Flash chromatography (Merck Silica gel 60, 230–400 mesh, 2/1 hexanes/ethyl acetate) afforded 2-biphenyl-4-yl-3-cyclopentylpropionic acid (5.13 g, 74%) as a white solid: mp 131–133° C.; FAB-HRMS m/e calcd for $C_{20}H_{22}O_2$ (M+H)$^+$ 294.1620, found 294.1626.

A solution of 2-biphenyl-4-yl-3-cyclopentylpropionic acid (121.0 mg, 0.41 mmol), benzotriazol-1-yloxytris (dimethylamino)phosphonium hexafluorophosphate (218.1 mg, 0.49 mmol), triethylamine (172 μL, 1.23 mmol), and 2-aminothiazole (45.3 mg, 0.45 mmol) in dry N,N-dimethylformamide (1 mL) was stirred at 25° C. under nitrogen for 24 h. The reaction mixture was concentrated in vacuo to remove N,N-dimethylformamide. The resulting residue was diluted with ethyl acetate (100 mL). The organic layer was washed with a 10% aqueous hydrochloric acid solution (1×100 mL), water (1×100 mL), and a saturated aqueous sodium chloride solution (1×100 mL). The organic layer was dried over sodium sulfate, filtered, and concentrated in vacuo. Flash chromatography (Merck Silica gel 60, 70–230 mesh, 9/1 to 3/1 hexanes/ethyl acetate gradient elution) afforded 2-biphenyl-4-yl-3-cyclopentyl-N-thiazol-2-yl-propionamide (102.2 mg, 66%) as a white solid: mp 194–195° C.; EI-HRMS m/e calcd for $C_{23}H_{24}N_2OS$ (M$^+$) 376.1609, found 376.1612.

In an analogous manner, there were obtained:

From 2-biphenyl-4-yl-3-cyclopentylpropionic acid and methyl 2-amino-4-thiazoleacetate: [2-(2-Biphenyl-4-yl-3-cyclopentyl-propionylamino)-thiazol-4-yl]-acetic acid methyl ester as a white foam: mp 57–58° C.; FAB-HRMS m/e calcd for $C_{26}H_{28}N_2O_3S$ (M+H)$^+$ 449.1899, found 449.1897.

From 2-biphenyl-4-yl-3-cyclopentylpropionic acid and ethyl 2-amino-4-thiazoleglyoxylate: [2-(2-Biphenyl-4-yl-3-cyclopentyl-propionylamino)-thiazol-4-yl]-oxo-acetic acid ethyl ester as a yellow glass: mp 87–88° C.; FAB-HRMS m/e calcd for $C_{27}H_{28}N_2O_4S$ (M+H)$^+$ 477.1848, found 477.1842.

From 2-biphenyl-4-yl-3-cyclopentylpropionic acid and ethyl 2-amino-4-thiazoleacetate: [2-(2-Biphenyl-4-yl-3-cyclopentyl-propionylamino)-thiazol-4-yl]-acetic acid ethyl ester as a white foam: mp 78–80° C.; FAB-HRMS m/e calcd for $C_{27}H_{30}N_2O_3S$ (M+H)$^+$ 463.2055, found 463.2052.

From 2-biphenyl-4-yl-3-cyclopentylpropionic acid and 2-amino-thiazole-4-carboxylic acid ethyl ester: 2-(2-Biphenyl-4-yl-3-cyclopentyl-propionylamino)-thiazole-4-carboxylic acid ethyl ester as a white solid: mp 81–84° C.; FAB-HRMS m/e calcd for for $C_{26}H_{28}N_2O_3S$ (M+H)$^+$ 449.1899, found 449.1885.

EXAMPLE 2

2-(2-Biphenyl-4-yl-3-cyclopentyl-propionylamino)-thiazole-4-carboxylic acid methyl ester

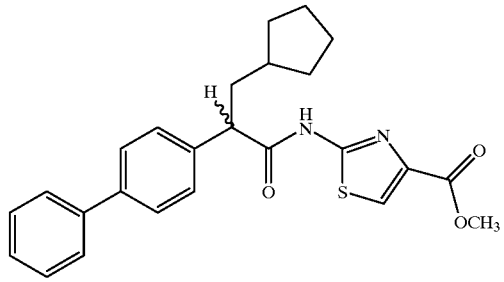

A solution of 2-(2-biphenyl-4-yl-3-cyclopentyl-propionylamino)-thiazole-4-carboxylic acid ethyl ester (prepared in Example 1B-d, 200 mg, 0.45 mmol) in methanol (4 mL) was treated with concentrated sulfuric acid (2 drops). The reaction mixture was heated under reflux for 15 h. The reaction mixture was allowed to cool to 25° C. and then concentrated in vacuo to remove methanol. The resulting residue was partitioned between water and ethyl acetate. The organic layer was dried over magnesium sulfate, filtered, and concentrated in vacuo. Flash chromatography (Merck Silica gel 60, 230–400 mesh, 2/1 hexanes/ethyl acetate) afforded 2-(2-biphenyl-4-yl-3-cyclopentyl-propionylamino)-thiazole-4-carboxylic acid methyl ester (80 mg, 41%) as a white solid: mp 98–101° C.; FAB-HRMS m/e calcd for $C_{25}H_{26}N_2O_3S$ $(M+H)^+$ 435.1743, found 435.1752.

EXAMPLE 3

2-Biphenyl-4-yl-3-cyclopentyl-N-(4-hydroxymethyl-thiazol-2-yl)-propionamide

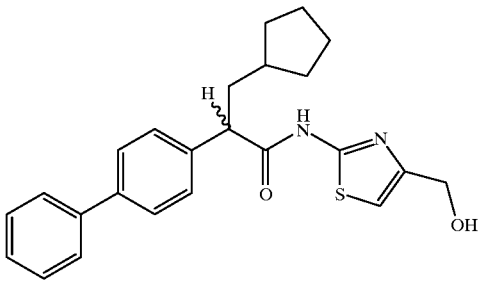

A solution of 2-(2-biphenyl-4-yl-3-cyclopentyl-propionylamino)-thiazole-4-carboxylic acid ethyl ester (prepared in Example 1B-d, 150 mg, 0.33 mmol) in diethyl ether (3 mL) at 0° C. under nitrogen was slowly treated with lithium aluminum hydride powder (16 mg, 0.44 mmol). The resulting reaction mixture continued to stir at 0° C. and was then allowed to gradually warm to 25° C. The reaction mixture was then stirred at 25° C. over a period of 64 h. The reaction mixture was slowly quenched by the dropwise addition of water (5 mL). The resulting reaction mixture was partitioned between water and ethyl acetate, and the layers were separated. The aqueous layer was further extracted with ethyl acetate (1×25 mL). The combined organic extracts were dried over magnesium sulfate, filtered, and concentrated in vacuo. Flash chromatography (Merck Silica gel 60, 230–400 mesh, 1/2 hexanes/ethyl acetate) afforded 2-biphenyl-4-yl-3-cyclopentyl-N-(4-hydroxymethyl-thiazol-2-yl)-propionamide (65 mg, 48%) as a white solid: mp 102–104° C.; EI-HRMS m/e calcd for $C_{24}H_{26}N_2O_2S$ $(M^+)$ 406.1715, found 406.1711.

In an analogous manner, there was obtained:

From [2-(2-biphenyl-4-yl-3-cyclopentyl-propionylamino)-thiazol-4-yl]-acetic acid ethyl ester: 2-Biphenyl-4-yl-3-cyclopentyl-N-[4-(2-hydroxyethyl)-thiazol-2-yl]-propionamide as a clear glass: mp 58–59° C.; EI-HRMS m/e calcd for $C_{25}H_{28}N_2O_2S$ $(M^+)$ 420.1872, found 420.1862.

EXAMPLE 4

(2R)-2-Biphenyl-4-yl-3-cyclopentyl-N-thiazol-2-yl-propionamide

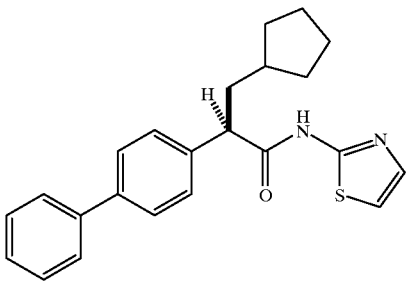

A solution of 2-biphenyl-4-yl-3-cyclopentylpropionic acid (prepared in Example 1A, 1.12 g, 3.80 mmol) in dry tetrahydrofuran (36 mL) under nitrogen was cooled to −78° C. and then treated with triethylamine (606 mL, 4.35 mmol). The reaction mixture was stirred at −78° C. for 15 min and then treated dropwise with trimethylacetyl chloride (491 mL, 3.98 mmol). The resulting reaction mixture was stirred at −78° C. for 15 min, at which time, the cooling bath was removed, and the reaction mixture was allowed to warm to 25° C. where it was stirred for 45 min. At this time, the reaction mixture was cooled back to −78° C. for the addition of the chiral auxiliary. Into a separate reaction flask, a solution of (4S)-(−)-4-isopropyl-2-oxazolidinone (467.9 mg, 3.62 mmol) in dry tetrahydrofuran (18 mL) under nitrogen was cooled to −78° C. and then treated with a 2.5M solution of n-butyllithium in hexanes (1.6 mL, 3.80 mmol). After complete addition of the n-butyllithium, the reaction mixture was allowed to warm to 25° C. where it was stirred for 1 h. This cloudy white solution was then added dropwise by syringe to the previously cooled (−78° C.) pivalate solution. The resulting reaction mixture was stirred at −78° C. for 1 h and then allowed to gradually warm to 25° C. The reaction mixture was stirred at 25° C. for 15 h. The resulting reaction mixture was quenched with a saturated aqueous sodium bisulfite solution and concentrated in vacuo to remove tetrahydrofuran. The resulting aqueous residue was diluted with ethyl acetate (150 mL). The organic layer was washed with a saturated aqueous sodium chloride solution (1×100 mL), dried over sodium sulfate, filtered, and concentrated in vacuo. Flash chromatography (Merck Silica gel 60, 230–400 mesh, 19/1 to 17/3 hexanes/ethyl acetate gradient elution) afforded the higher $R_f$ product 3-{2(S)-biphenyl-4-yl-3-cyclopentyl-propionyl}-4(S)-isopropyl-oxazolidin-2-one (679.2 mg, 92%) as a yellow oil: EI-HRMS m/e calcd for $C_{26}H_{31}NO_3$ $(M^+)$ 405.2304, found 405.2310; and the lower $R_f$ product 3-{2(R)-biphenyl-4-yl-3-cyclopentyl-propionyl}-4(S)-isopropyl-oxazolidin-2-one (127.4 mg, 17%) as a yellow oil: EI-HRMS m/e calcd for $C_{26}H_{31}NO_3$ $(M^+)$ 405.2304, found 405.2313.

A solution of 3-{2(R)-biphenyl-4-yl-3-cyclopentyl-propionyl}-4(S)-isopropyl-oxazolidin-2-one (127.4 mg, 0.31 mmol) in tetrahydrofuran (1.3 ml,) and water (300 μL) was cooled to 0° C. and then sequentially treated with a 30% aqueous hydrogen peroxide solution (39 μL, 1.25 mmol ) and an 0.8M aqueous lithium hydroxide solution (628 μL, 0.50 mmol). The reaction mixture was allowed to warm to 25° C. where it was stirred for 7 h. At this time, the reaction mixture was treated with solution of sodium sulfite (158.4 mg, 1.26 mmol) in water (952 μL). The reaction mixture was stirred at 0° C. for 30 min and then concentrated in vacuo to remove tetrahydrofuran. The resulting aqueous layer was extracted with diethyl ether (1×100 mL). The aqueous layer was then acidified to pH=1 with a 10% aqueous hydrochloric acid solution and extracted with ethyl acetate (1×100 mL). The organic extract was washed with water, dried over sodium sulfate, filtered, and concentrated in vacuo. Flash chromatography (Merck Silica gel 60, 230–400 mesh, 1/1 hexanes/ethyl acetate) afforded 2(R)-biphenyl-4-yl-3-cyclopentylpropionic acid (43 mg, 46%) as a white solid: mp 136–137° C.; EI-HRMS m/e calcd for $C_{20}H_{22}O_2$ (M$^+$) 294.1620, found 294.1618.

A solution of 2(R)-biphenyl-4-yl-3-cyclopentylpropionic acid (36.9 mg, 0.13 mmol), O-benzotriazol-1-yl-N,N,N',N'-tetramethyluronium hexafluorophosphate (52.3 mg, 0.14 mmol), N,N-diisopropylethylamine (66 μL, 0.38 mmol), and 2-aminothiazole (25.1 mg, 0.25 mmol) in dry N,N-dimethylformamide (627 μL) was stirred at 25° C. under nitrogen for 13 h. The reaction mixture was concentrated in vacuo to remove the N,N-dimethylformamide. The resulting residue was diluted with ethyl acetate (100 mL). The organic layer was washed with a 10% aqueous hydrochloric acid solution (1×100 mL), a saturated aqueous sodium bicarbonate solution (1×100 mL), and a saturated aqueous sodium chloride solution (1×100 mL). The organic layer was dried over sodium sulfate, filtered, and concentrated in vacuo. Flash chromatography (Merck Silica gel 60, 70–230 mesh, 3/1 hexanes/ethyl acetate) afforded (2R)-2-biphenyl-4-yl-3-cyclopentyl-N-thiazol-2-yl-propionamide (29.4 mg, 62%) as a white foam: mp 132–134° C.; FAB-HRMS m/e calcd for $C_{23}H_{24}N_2OS$ (M+H)$^+$ 377.1687, found 377.1696.

EXAMPLE 5

3-Cyclopentyl-2-(4-naphthalen-1-yl-phenyl)-N-thiazol-2-yl-propionamide

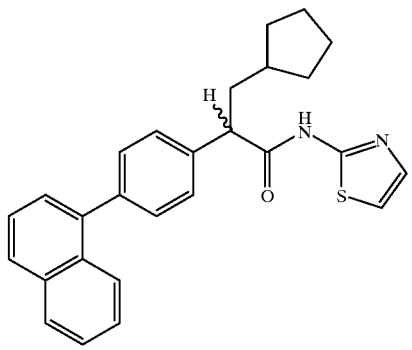

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M$^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M$^+$) 358.0430, found 358.0434.

A solution of 3-cyclopentyl-2-(4-iodo-phenyl)-propionic acid methyl ester (3.87 g, 10.81 mmol), 1-naphthaleneboronic acid (2.79 g, 16.22 mmol), triethylamine (4.5 mL, 32.44 mmol), palladium (II) acetate (72.8 mg, 0.324 mmol), and tri-o-tolylphosphine (204.1 mg, 0.670 mmol) in dry N,N-dimethylformamide (43 mL) was heated at 100° C. under nitrogen for 1 h. The reaction mixture was allowed to cool to 25° C. and then concentrated in vacuo to remove N,N-dimethylformamide. The residue was diluted with ethyl acetate (200 mL). The organic phase was washed with a saturated aqueous sodium bicarbonate solution (1×100 mL) and water (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-naphthalen-1-yl-phenyl)-propionic acid methyl ester (3.51 g, 90%) as a yellow oil: EI-HRMS m/e calcd for $C_{25}H_{26}O_2$ (M$^+$) 358.1933, found 358.1930.

A solution of 3-cyclopentyl-2-(4-naphthalen-1-yl-phenyl)-propionic acid methyl ester (3.32 g, 9.26 mmol) in tetrahydrofuran (12 mL) was treated with a 0.8M aqueous lithium hydroxide solution (12 mL). The resulting reaction mixture was stirred at 25° C. for 24 h, at which time, thin layer chromatography indicated the presence of starting material. The reaction mixture was then heated at 80° C. for 18 h. The reaction mixture was then allowed to cool to 25° C. and concentrated in vacuo to remove tetrahydrofuran. The residue was acidified to pH=2 with a 10% aqueous hydrochloric acid solution and then extracted with ethyl acetate (2×150 mL). The combined organic extracts were dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-naphthalen-1-yl-phenyl)-propionic acid (1.74 g, 55%) as a white foam: mp 63–64° C.; EI-HRMS m/e calcd for $C_{24}H_{24}O_2$ (M$^+$) 344.1776, found 344.1770.

A solution of 3-cyclopentyl-2-(4-naphthalen-1-yl-phenyl)-propionic acid (100 mg, 0.29 mmol) in dry N,N-dimethylformamide (2 ml,) was treated with O-benzotriazol-1-yl-N,N,N',N'-tetramethyluronium hexafluorophosphate (110 mg, 0.29 mmol), N,N-diisopropylethylamine (61 μL, 0.35 mmol), and 2-aminothiazole (45 mg, 0.44 mmol). The reaction mixture was stirred at 25° C. under nitrogen for 15 h. The reaction mixture was poured into a mixture of water and ethyl acetate (1:1), and the layers were separated. The organic layer was washed with a 1N aqueous hydrochloric acid solution and a saturated aqueous sodium chloride solution. The organic layer was dried over magnesium sulfate, filtered, and concentrated in vacuo. Flash chromatography (Merck Silica gel 60, 70–230 mesh, 2/1 hexanes/ethyl acetate) afforded 3-cyclopentyl-2-(4-naphthalen-1-yl-phenyl)-N-thiazol-2-yl-propionamide (92 mg, 74%) as a white foam: mp 202–204° C.; FAB-HRMS m/e calcd for $C_{27}H_{26}N_2OS$ (M+H)$^+$ 427.1844, found 427.1837.

In an analogous manner, there were obtained:

From 3-cyclopentyl-2-(4-naphthalen-1-yl-phenyl)-propionic acid and methyl 2-amino-4-thiazoleacetate: {2-[3-Cyclopentyl-2-(4-naphthalen-1-yl-phenyl)-propionylamino]-thiazol-4-yl}-acetic acid methyl ester as a white foam: mp 65–69° C.; EI-HRMS m/e calcd for $C_{30}H_{30}N_2O_3S$ (M$^+$) 498.1977, found 498.1982.

From 3-cyclopentyl-2-(4-naphthalen-1-yl-phenyl)-propionic acid and ethyl 2-amino-4-thiazoleacetate: {2-[3-Cyclopentyl-2-(4-naphthalen-1-yl-phenyl)-propionylamino]-thiazol-4-yl}-acetic acid ethyl ester as a white foam: mp 63–68° C.; EI-HRMS m/e calcd for $C_{31}H_{32}N_2O_3S$ (M$^+$) 512.2134, found 512.2136.

From 3-cyclopentyl-2-(4-naphthalen-1-yl-phenyl)-propionic acid and 2-amino-thiazole-4-carboxylic acid methyl ester: 2-[3-Cyclopentyl-2-(4-naphthalen-1-yl-phenyl)-propionylamino]-thiazole-4-carboxylic acid methyl ester as a white foam: mp 103–107° C.; EI-HRMS m/e calcd for $C_{29}H_{28}N_2O_3S$ (M$^+$) 484.1821, found 484.1825.

From 3-cyclopentyl-2-(4-naphthalen-1-yl-phenyl)-propionic acid and 2-amino-4-(hydroxymethyl)thiazole hydrochloride: 3-Cyclopentyl-N-(4-hydroxymethyl-thiazol-2-yl)-2-(4-naphthalen-1-yl-phenyl)-propionamide as a white foam: mp 90–93° C.; EI-HRMS m/e calcd for $C_{28}H_{28}N_2O_2S$ (M$^+$) 456.1872, found 456.1867.

EXAMPLE 6

3-Cyclopentyl-N-[4-(2-hydroxyethyl)-thiazol-2-yl]-2-(4-naphthalen-1-yl-phenyl)-propionamide

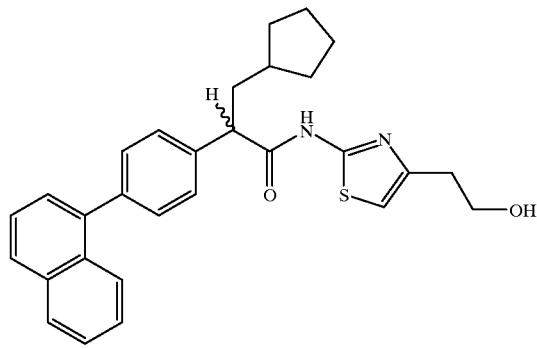

A solution of {2-[3-cyclopentyl-2-(4-naphthalen-1-yl-phenyl)-propionylamino]-thiazol-4-yl}-acetic acid ethyl ester (prepared in Example 5B-b, 60 mg, 0.117 mmol) in diethyl ether (1 mL) was cooled to 0° C. and then slowly treated with lithium aluminum hydride powder (6.7 mg, 0.176 mmol). The reaction mixture was stirred at 0° C. for 30 min, at which time, thin layer chromatography showed the absence of starting material. The reaction mixture was slowly quenched by the dropwise addition of a saturated aqueous sodium bicarbonate solution (2 mL). The resulting reaction mixture was treated with ethyl acetate (2 mL) and allowed to stir at 25° C. for 15 h. The two-phase reaction mixture was then partitioned between water (20 mL) and ethyl acetate (20 mL), and the layers were separated. The aqueous layer was further extracted with ethyl acetate (1×20 mL). The combined organic extracts were dried over magnesium sulfate, filtered, and concentrated in vacuo. Flash chromatography (Merck Silica gel 60, 230–400 mesh, 1/2 hexanes/ethyl acetate) afforded 3-cyclopentyl-N-[4-(2-hydroxyethyl)-thiazol-2-yl]-2-(4-naphthalen-1-yl-phenyl)-propionamide (19 mg, 34%) as a yellow foam: mp 84–87° C.; EI-HRMS m/e calcd for $C_{29}H_{30}N_2O_2S$ (M$^+$) 470.2028, found 470.2020.

EXAMPLE 7

3-Cyclopentyl-N-thiazol-2-yl-2-(4-thiophen-2-yl-phenyl)-propionamide

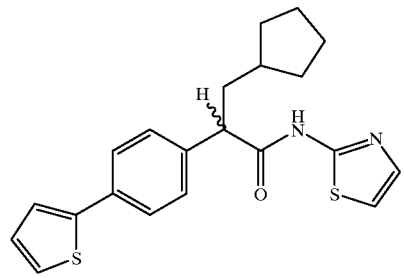

A solution of diisopropylamine (7.7 mL, 54.88 mmol) in dry tetrahydrofuran (23 mL) and 1,3-dimethyl-3,4,5,6-tetrahydro-2(1H)-pyrimidinone (10 mL) was cooled to −78° C. under nitrogen and then treated with a 2.5M solution of n-butyllithium in hexanes (22.0 mL, 54.88 mmol). The reaction mixture was stirred at −78° C. for 30 min and then treated dropwise with a solution of 4-bromophenylacetic acid (5.62 g, 26.13 mmol) in dry tetrahydrofuran (23 mL) and 1,3-dimethyl-3,4,5,6-tetrahydro-2(1H)-pyrimidinone (10 mL). The reaction mixture turned dark in color and was allowed to stir at −78° C. for 1 h, at which time, a solution of iodomethylcyclopentane (5.76 g, 27.44 mmol) in a small amount of dry tetrahydrofuran was added dropwise. The reaction mixture was allowed to warm to 25° C. where it was stirred for 24 h. The reaction mixture was quenched with water and then concentrated in vacuo to remove tetrahydrofuran. The aqueous residue was acidified using a 10% aqueous hydrochloric acid solution. The resulting aqueous layer was extracted with ethyl acetate (2×100 mL). The combined organic extracts were dried over sodium sulfate, filtered, and concentrated in vacuo. Flash chromatography (Merck Silica gel 60, 230–400 mesh, 3/1 hexanes/ethyl acetate) afforded 2-(4-bromo-phenyl)-3-cyclopentyl-propionic acid (3.88 g, 50%) as a light yellow solid: mp 91–93° C.; EI-HRMS m/e calcd for $C_{14}H_{17}BrO_2$ (M$^+$) 296.0412, found 296.0417.

A solution of 2-(4-bromo-phenyl)-3-cyclopentyl-propionic acid (1.01 g, 3.39 mmol) in methylene chloride (8.5 mL) was treated with dry N,N-dimethylformamide (2 drops). The reaction mixture was cooled to 0° C. and then treated with oxalyl chloride (3 mL, 33.98 mmol). The reaction mixture was stirred at 0° C. for 10 min and then stirred at 25° C. for 15 h. The reaction mixture was concentrated in vacuo. The resulting yellow oil was dissolved in a small amount of methylene chloride and slowly added to a cooled solution (0° C.) of 2-aminothiazole (680.6 mg, 6.79 mmol) and N,N-diisopropylethylamine (1.2 mL, 6.79 mmol) in methylene chloride (17 mL). The resulting reaction mixture was stirred at 0° C. for 10 min and then at 25° C. for 15 h. The reaction mixture was concentrated in vacuo to remove methylene chloride. The resulting residue was diluted with ethyl acetate (200 mL). The organic phase was washed with a 10% aqueous hydrochloric acid solution (2×100 mL), a saturated aqueous sodium bicarbonate solution (2×100 mL), and a saturated aqueous sodium chloride solution (1×100 mL). The organic layer was then dried over sodium sulfate, filtered, and concentrated in vacuo to afford 2-(4-bromo-phenyl)-3-cyclopentyl-N-thiazol-2-yl-propionamide (1.23 g, 95%) as an orange solid which was used in subsequent reactions without further purification. An analytical sample was recrystallized from ethyl acetate to provide a cream solid: mp 201–202° C.; EI-HRMS m/e calcd for $C_{17}H_{19}BrN_2OS$ ($M^+$) 378.0401, found 378.0405.

A mixture of 2-(4-bromo-phenyl)-3-cyclopentyl-N-thiazol-2-yl-propionamide (102.5 mg, 0.27 mmol), tetrakis(triphenylphosphine)palladium(0) (15.6 mg, 0.014 mmol), 2-thiopheneboronic acid (69.2 mg, 0.54 mmol), and a 2M aqueous sodium carbonate solution (405 µL, 0.81 mmol) in 1,2-dimethoxyethane (9 mL) was heated under reflux for 24 h. The reaction mixture was allowed to cool to 25° C. and then filtered to remove the catalyst. The filtrate was concentrated in, vacuo. Flash chromatography (Merck Silica gel 60, 230–400 mesh, 3/1 hexanes/ethyl acetate) afforded 3-cyclopentyl-N-thiazol-2-yl-2-(4-thiophen-2-yl-phenyl)-propionamide (4.5 mg, 4%) as a yellow solid: mp 194° C. (dec); EI-HRMS m/e calcd for $C_{21}H_{22}N_2OS_2$ ($M^+$) 382.1174, found 382.1175.

EXAMPLE 8

3-Cyclopentyl-2-(4-pyridin-3-yl-phenyl)-N-thiazol-2-yl-propionamide

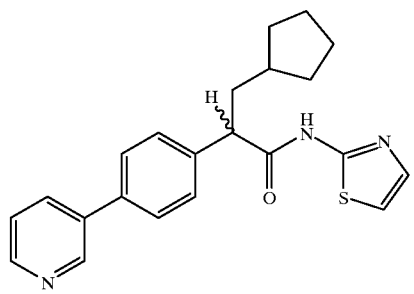

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ ($M^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a solution of pyridine-3-boronic acid (515 mg, 4.19 mmol) and a 2M aqueous sodium carbonate solution (2.8 mL, 5.58 mmol) in water (5 mL). The resulting reaction mixture was heated under reflux for 90 min. The reaction mixture was allowed to cool to 25° C. and then filtered to remove the catalyst. The filtrate was partitioned between water and methylene chloride, and the layers were separated. The aqueous layer was further extracted with methylene chloride (75 mL). The combined organic extracts were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-pyridin-3-yl-phenyl)-propionic acid methyl ester (800 mg, 92%) as a brown oil: EI-HRMS m/e calcd for $C_{20}H_{23}NO_2$ ($M^+$) 309.1729, found 309.1728.

A solution of 3-cyclopentyl-2-(4-pyridin-3-yl-phenyl)-propionic acid methyl ester (450 mg, 1.45 mmol) in tetrahydrofuran (5 mL) was treated with a 0.8M aqueous lithium hydroxide solution (2.18 mL, 1.74 mmol). The resulting reaction mixture was stirred at 25° C. for 3 d. The reaction mixture was then partitioned between water (50 mL) and ethyl acetate (50 mL), and the layers were separated. The aqueous layer was further extracted with ethyl acetate (2×50 mL). The combined organic extracts were dried over magnesium sulfate, filtered, and concentrated in vacuo. The resulting solid was purified by precipitation from methylene chloride/ethyl acetate to afford 3-cyclopentyl-2-(4-pyridin-3-yl-phenyl)-propionic acid (271 mg, 63%) as a white solid: mp 136–138° C.; EI-HRMS m/e calcd for $C_{19}H_{21}NO_2$ ($M^+$) 295.1572, found 295.1572.

A solution of triphenylphosphine (160 mg, 0.61 mmol) in methylene chloride (4 mL) was cooled to 0° C. and then slowly treated with N-bromosuccinimide (109 mg, 0.61 mmol). The reaction mixture was stirred at 0° C. for 30 min and then treated with 3-cyclopentyl-2-(4-pyridin-3-yl-phenyl)-propionic acid (150 mg, 0.51 mmol). The resulting reaction mixture was stirred at 0° C. for 5 min and then allowed to warm to 25° C. where it was stirred for 30 min. The reaction mixture was then treated with 2-aminothiazole (112 mg, 1.12 mmol). The resulting reaction mixture was stirred at 25° C. for 15 h. The crude reaction mixture was then directly purified by flash chromatography (Merck Silica gel 60, 230–400 mesh, 100% diethyl ether then 1/1 diethyl ether/ethyl acetate then 1/3 diethyl ether/ethyl acetate) to afford 3-cyclopentyl-2-(4-pyridin-3-yl-phenyl)-N-thiazol-2-yl-propionamide (15 mg, 8%) as a pale yellow foam: mp 48–52° C.; EI-HRMS m/e calcd for $C_{22}H_{23}N_3OS$ (M$^+$) 377.1562, found 377.1564.

EXAMPLE 9

3-Cyclopentyl-2-(4-pyridin-4-yl-phenyl)-N-thiazol-2-yl-propionamide

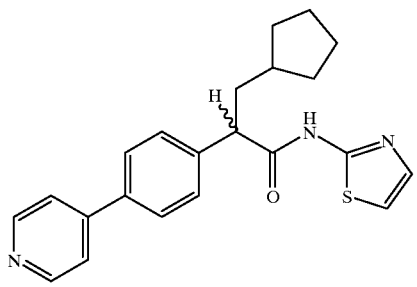

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M$^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M$^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a solution of pyridine-4-boronic acid (515 mg, 4.19 mmol) and a 2M aqueous sodium carbonate solution (2.8 mL, 5.58 mmol) in water (5 mL). The resulting reaction mixture was heated under reflux for 8 h. The reaction mixture was allowed to cool to 25° C. where it was stirred for 3 d. The reaction mixture was partitioned between water (75 mL) and methylene chloride (75 mL), and the layers were separated. The aqueous layer was further extracted with methylene chloride (75 mL). The combined organic extracts were dried over magnesium sulfate, filtered, and concentrated in vacuo to afford 3-cyclopentyl-2-(4-pyridin-4-yl-phenyl)-propionic acid methyl ester (240 mg, 28%) as a brown oil that was used without further purification and characterization.

A solution of 3-cyclopentyl-2-(4-pyridin-4-yl-phenyl)-propionic acid methyl ester (240 mg, 0.78 mmol) in tetrahydrofuran (3 mL) was treated with a 0.8M aqueous lithium hydroxide solution (1.45 mL, 1.16 mmol). The resulting reaction mixture was stirred at 25° C. for 30 min and then heated under reflux for 15 h. The reaction mixture was allowed to cool to 25° C. and then partitioned between water (100 mL) and ethyl acetate (70 mL). The layers were separated, and the aqueous layer was further extracted with ethyl acetate (1×30 mL). The combined organic extracts were dried over magnesium sulfate, filtered, and concentrated in vacuo to afford a yellow oil that solidified upon sitting. The solid was collected to afford 3-cyclopentyl-2-(4-pyridin-4-yl-phenyl)-propionic acid (127 mg, 55%) as a yellow solid: mp 118–121° C.; FAB-HRMS m/e calcd for $C_{19}H_{21}NO_2$ (M+H)$^+$ 296.1650, found 296.1658.

A solution of triphenylphosphine (59 mg, 0.22 mmol) in methylene chloride (1 mL) was cooled to 0° C. and then slowly treated with N-bromosuccinimide (39 mg, 0.22 mmol). The reaction mixture was stirred at 0° C. for 20 min and then treated with 3-cyclopentyl-2-(4-pyridin-4-yl-phenyl)-propionic acid (55 mg, 0.19 mmol). The resulting reaction mixture was stirred at 0° C. for 10 min and then allowed to warm to 25° C. where it was stirred for 20 min. The reaction mixture was then treated with 2-aminothiazole (41 mg, 0.41 mmol). The resulting reaction mixture was stirred at 25° C. for 15 h. The crude reaction mixture was then directly purified by flash chromatography (Merck Silica gel 60, 230–400 mesh, 20/1 methylene chloride/methanol) to afford impure 3-cyclopentyl-2-(4-pyridin-4-yl-phenyl)-N-thiazol-2-yl-propionamide as an orange foam. The impure foam was treated with a solution of hexanes/ethyl acetate (5 mL, 1:3), and a precipitate formed. The reaction mixture was placed in the freezer for 15 h, and the solid was collected by filtration to afford 3-cyclopentyl-2-(4-pyridin-4-yl-phenyl)-N-thiazol-2-yl-propionamide (26 mg, 37%) as a pale orange solid: mp 213–215° C.; EI-HRMS m/e calcd for $C_{22}H_{23}N_3OS$ (M$^+$) 377.1562, found 377.1564.

EXAMPLE 10

3-Cyclopentyl-2-[4-(1H-indol-5-yl)-phenyl]-N-thiazol-2-yl-propionamide

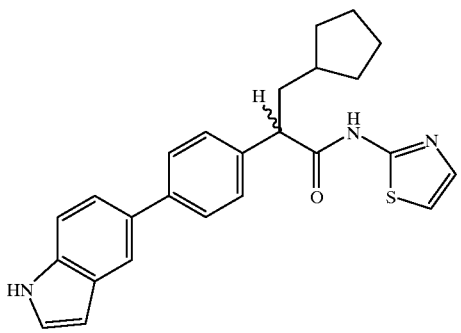

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ ($M^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a mixture of 5-indolylboronic acid (670 mg, 4.19 mmol) in water (5 mL) and a 2M aqueous sodium carbonate solution (2.8 mL, 5.58 mmol). The resulting reaction mixture was heated under reflux for 2 h. The reaction mixture was allowed to cool to 25° C. and then filtered to remove the catalyst. The filtrate was partitioned between water (50 mL) and methylene chloride (50 mL), and the layers were separated. The aqueous layer was further extracted with methylene chloride (50 mL). The combined organic extracts were dried over magnesium sulfate, filtered, and concentrated in vacuo. Flash chromatography (Merck Silica gel 60, 230–400 mesh, 1/2 hexanes/ethyl acetate) afforded 3-cyclopentyl-2-[4-(1H-indol-5-yl)-phenyl]-propionic acid methyl ester (347 mg, 36%) as a light brown oil: EI-HRMS m/e calcd for $C_{23}H_{25}NO_2$ ($M^+$) 347.1885, found 347.1887.

A solution of 3-cyclopentyl-2-[4-(1H-indol-5-yl)-phenyl]-propionic acid methyl ester (310 mg, 0.89 mmol) in tetrahydrofuran (2 mL) was treated with a 0.8M aqueous lithium hydroxide solution (1.45 mL, 1.16 mmol). The resulting reaction mixture was stirred at 25° C. for 39 h and then heated at 80° C. for 4 h. The reaction mixture was then allowed to cool to 25° C. where it was stirred for 3 d. The reaction mixture was then concentrated in vacuo to remove tetrahydrofuran. The resulting aqueous layer was extracted with methylene chloride (2×40 mL). The combined organic extracts were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-[4-(1H-indol-5-yl)-phenyl]-propionic acid (170 mg, 58%) as a pale yellow foam: mp 62–65° C.; FAB-HRMS m/e calcd for $C_{22}H_{23}NO_2$ $(M+H)^+$ 333.1729, found 333.1731.

A solution of triphenylphosphine (71 mg, 0.27 mmol) in methylene chloride (1.5 mL) was cooled to 0° C. and then slowly treated with N-bromosuccinimide (48 mg, 0.27 mmol). The reaction mixture was stirred at 0° C. for 25 min and then treated with 3-cyclopentyl-2-[4-(1H-indol-5-yl)-phenyl]-propionic acid (75 mg, 0.23 mmol). The resulting reaction mixture was stirred at 0° C. for 5 min and then allowed to warm to 25° C. where it was stirred for 30 min. The reaction mixture was then treated with 2-aminothiazole (50 mg, 0.50 mmol). The resulting reaction mixture was stirred at 25° C. for 5 d. The crude reaction mixture was then directly purified by flash chromatography (Merck Silica gel 60, 230–400 mesh, 9/1 chloroform/methanol) to afford impure 3-cyclopentyl-2-[4-(1H-indol-5-yl)-phenyl]-N-thiazol-2-yl-propionamide. Repurification by flash chromatography (Merck Silica gel 60, 230–400 mesh, 1/3 hexanes/ethyl acetate) afforded pure 3-cyclopentyl-2-[4-(1H-indol-5-yl)-phenyl]-N-thiazol-2-yl-propionamide (8 mg, 9%) as a white solid: mp 112–115° C.; EI-HRMS m/e calcd for $C_{25}H_{25}N_3OS$ ($M^+$) 415.1718, found 415.1714.

EXAMPLE 11

2-(4-Benzyloxy-phenyl)-3-cyclopentyl-N-thiazol-2-yl-propionamide

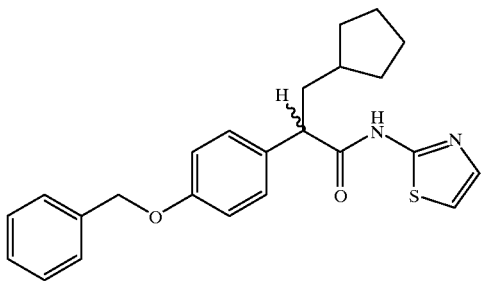

A mixture of (4-hydroxy-phenyl)-acetic acid methyl ester (5.0 g, 30.0 mmol) and potassium carbonate (5.0 g, 36.1 mmol) in acetone (10 mL) was treated with benzyl bromide (4.29 mL, 36.1 mmol). The reaction mixture was then heated at 90° C. for 6 h. At this time, the potassium carbonate was removed by filtration. The filtrate was concentrated in vacuo. Flash chromatography (Merck Silica gel 60, 230–400 mesh, 95/5 hexanes/ethyl acetate) afforded (4-benzyloxy-phenyl)-acetic acid methyl ester (7.1 g, 92.1%) as a clear oil: EI-HRMS m/e calcd for $C_{16}H_{16}O_3$ (M+) 256.1099 found 256.1103.

A solution of freshly prepared lithium diisopropylamide (23 mL of a 0.31M stock solution, 7.13 mmol) was cooled to −78° C. and then treated with a solution of (4-benzyloxy-phenyl)-acetic acid methyl ester (1.66 g, 6.48 mmol) in tetrahydrofuran/1,3-dimethyl-3,4,5,6-tetrahydro-2(1H)-pyrimidinone (16.1 mL, 3:1). The resulting solution was stirred at −78° C. for 45 min. At this time, the reaction was treated with a solution of iodomethylcyclopentane (1.50 g, 7.13 mmol) in 1,3-dimethyl-3,4,5,6-tetrahydro-2(1H)-pyrimidinone (2 mL). The reaction mixture was stirred at −78° C. for 4 h. The reaction was then warmed to 25° C. and was stirred at 25° C. for 48 h. At this time, the reaction mixture was quenched by the dropwise addition of a saturated aqueous ammonium chloride solution (10 mL). This mixture was poured into water (100 mL) and extracted with ethyl acetate (3×50 mL). The combined organic extracts were washed with a saturated aqueous lithium chloride solution (1×100 mL), dried over sodium sulfate, filtered, and concentrated in vacuo. Flash chromatography (Merck Silica gel 60, 230–400 mesh, 98/2 hexanes/ethyl acetate) afforded 2-(4-benzyloxy-phenyl)-3-cyclopentyl-propionic acid methyl ester (1.90 g, 86.6%) as a white wax: mp 55–57° C.; EI-HRMS m/e calcd for $C_{22}H_{26}O_3$ (M+) 338.1881 found 228.1878.

A solution of 2-(4-benzyloxy-phenyl)-3-cyclopentyl-propionic acid methyl ester (1.38 g, 4.08 mmol) in tetrahydrofuran/water/methanol (10.2 ml, 3:1:1) was treated with a 2N aqueous sodium hydroxide solution (3.06 mL, 6.12 mmol). The reaction was stirred at 25° C. for 16 h. At this time, an additional amount of the 2N aqueous sodium hydroxide solution (3.06 mL, 6.12 mmol) was added. The reaction was stirred at 25° C. for an additional 24 h. At this time, the reaction mixture was poured into water and extracted into methylene chloride. The layers were separated. The aqueous layer was acidified to pH=1 with a 1N aqueous hydrochloric acid solution and was then extracted with a solution of methylene chloride/methano (90/10). The combined organic extracts were dried over sodium sulfate, filtered, and concentrated in vacuo. Flash chromatography (Merck Silica gel 60, 230–400 mesh, 50/50 hexanes/ethyl acetate) afforded 2-(4-benzyloxy-phenyl)-3-cyclopentyl-propionic acid (0.79 g, 60.2%) as a white solid: mp 112–114° C.

A solution of 2-(4-benzyloxy-phenyl)-3-cyclopentyl-propionic acid (0.15 g, 0.46 mmol) in methylene chloride (4.6 mL) was cooled to 0° C. and then treated with a 2.0M solution of oxalyl chloride in methylene chloride (0.25 mL, 0.50 mmol) and a few drops of N,N-dimethylformamide. The reaction mixture was stirred at 0° C. for 10 min and at 25° C. for 30 min. The reaction mixture was then treated with a solution of 2-aminothiazole (0.10 g, 1.01 mmol) and N,N-diisopropylethylamine (0.19 mL, 1.10 mmol) in tetrahydrofuran (2.3 mL). The reaction mixture was stirred at 25° C. for 18 h. At this time, the reaction was concentrated in vacuo. Flash chromatography (Merck Silica gel 60, 230–400 mesh 80/20 hexanes/ethyl acetate) afforded 2-(4-benzyloxy-phenyl)-3-cyclopentyl-N-thiazol-2-yl-propionamide (119.4 mg, 63.5%) as a white solid: mp 48–50° C.; EI-HRMS m/e calcd for $C_{24}H_{26}N_2O_2S$ (M+) 406.1715, found 406.1716.

EXAMPLE 12

3-Cyclopentyl-2-(4-phenoxy-phenyl)-N-thiazol-2-yl-propionamide

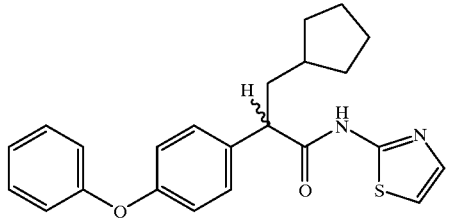

A solution of diisopropylamine (2.52 mL, 19.3 mmol) in tetrahydrofuran (50 mL) was cooled to −78° C. under a nitrogen atmosphere and then treated with a 2.5M solution of n-butyllithium in hexanes (7.7 mL, 19.3 mmol). The reaction mixture was stirred at −78° C. for 15 min and then slowly treated with a solution of 4-phenoxyphenylacetic acid (2.00 g, 8.8 mmol) in tetrahydrofuran (12 mL) and 1,3-dimethyl-3,4,5,6-tetrahydro-2(1H)-pyrimidinone (4 mL) via cannulation. The resulting bright yellow solution was allowed to stir for 1 h at −78° C. After this time, the reaction mixture was treated with a solution of iodomethylcyclopentane (2.02 g, 9.6 mmol) in 1,3-dimethyl-3,4,5,6-tetrahydro-2(1H)-pyrimidinone (1 mL) via cannulation. The resulting reaction mixture was stirred for 1 h at −78° C. and then allowed to warm to 25° C. where it was stirred for 14 h. The reaction was then acidified to pH=2 by the dropwise addition of a 1N aqueous hydrochloric acid solution and then extracted with ethyl acetate (3×25 mL). The combined organic extracts were dried over sodium sulfate, filtered, and concentrated in vacuo. Flash chromatography (Merck Silica gel 60, 230–400 mesh, 50/50 hexanes/ethyl acetate plus 1% acetic acid) afforded 3-cyclopentyl-2-(4-phenoxy-phenyl) propionic acid (2.49 g, 91%) as a white foam: EI-HRMS m/e calcd for $C_{20}H_{22}O_3$ (M+) 310.1568, found 310.1568.

A solution of 3-cyclopentyl-2-(4-phenoxy-phenyl)-propionic acid (50 mg, 0.16 mmol),benzotriazol-1-yloxy-tris(dimethylamino)phosphonium hexafluorophosphate (106 mg, 0.24 mmol), and 2-aminothiazole (21 mg, 0.24 mmol) in methylene chloride (10 mL) at 25° C. was treated with triethylamine (0.067 mL, 0.48 mmol). The reaction mixture was then stirred at 25° C. for 14 h. After this time, the reaction mixture was diluted with water (10 mL) and then extracted with methylene chloride (3×10 mL). The combined organic extracts were then washed with water (1×10 mL), a 1N aqueous sodium hydroxide solution (1×10 mL), and a 1N aqueous hydrochloric acid solution (1×10 mL). The organic layer was then dried over sodium sulfate, filtered, and concentrated in vacuo. Flash chromatography (Merck Silica gel 60, 230–400 mesh, 90/10 hexanes/ethyl acetate) afforded 3-cyclopentyl-2-(4-phenoxy-phenyl)-N-thiazol-2-yl-propionamide (48 mg, 76%) as an off-white solid: mp 154.9–155.1° C.; EI-HRMS m/e calcd for $C_{23}H_{24}O_2N_2S$ (M+) 392.1558, found 392.1546.

In an analogous manner, there was obtained:

From 3-cyclopentyl-2-(4-phenoxy-phenyl)propionic acid and 2-aminothiazol-4-yl-acetic acid ethyl ester: {2-[3-Cyclopentyl-2-(4-phenoxy-phenyl)-propionylamino]-thiazol-4-yl}-acetic acid ethyl ester as a white foam: FAB-HRMS m/e calcd for $C_{27}H_{30}N_2O_4S$ (M+H)+ 479.2004, found 479.2001.

EXAMPLE 13

3-Cyclopentyl-N-(4-hydroxymethyl-thiazol-2-yl)-2-(4-phenoxy-phenyl)-propionamide

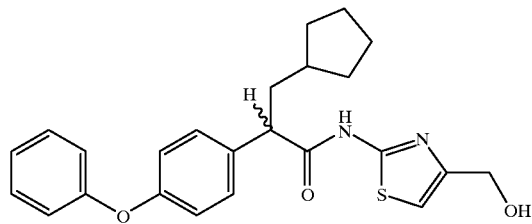

A solution of 3-cyclopentyl-2-(4-phenoxy-phenyl)-propionic acid (prepared in Example 12A, 767 mg, 2.47 mmol) in methylene chloride (20 mL) at 25° C. was treated with 2-amino-thiazole-4-carboxylic acid ethyl ester (553 mg, 3.21 mmol), benzotriazol-1-yloxytris(dimethylamino)phosphonium hexafluorophosphate (1.64 g, 3.71 mmol), and triethylamine (1 mL, 7.41 mmol). The resulting reaction mixture was stirred at 25° C. for 16 h. The reaction mixture was then diluted with water (10 mL) and then extracted with methylene chloride (3×15 mL). The combined organic extracts were washed with a 1N aqueous sodium hydroxide solution (1×10 mL), a 1N aqueous hydrochloric acid solution (1×10 mL), and a saturated aqueous sodium chloride solution (1×10 mL). The organic layer was then dried over sodium sulfate, filtered, and concentrated in vacuo. Flash chromatography (Merck Silica gel 60, 230–400 mesh, 90/10 hexanes/ethyl acetate) afforded 2-[3-cyclopentyl-2-(4-phenoxy-phenyl)-propionylamino]-thiazole-4-carboxylic acid ethyl ester (564 mg, 49%) as a white foam: FAB-HRMS m/e calcd for $C_{26}H_{28}N_2O_4S$ (M+H)+ 465.1848, found 465.1831.

A solution of 2-[3-cyclopentyl-2-(4-phenoxy-phenyl)-propionylamino]-thiazole-4-carboxylic acid ethyl ester (100 mg, 0.22 mmol) in diethyl ether (10 mL) was cooled to 0° C. and then treated with lithium aluminum hydride (13 mg, 0.32 mmol). The reaction mixture was slowly warmed to 25° C. where it was stirred for 16 h. After this time, the reaction mixture was slowly diluted with water (5 mL) and then extracted with ethyl acetate (3×10 mL). The combined organic extracts were dried over sodium sulfate, filtered, and concentrated in vacuo. Flash chromatography (Merck Silica gel 60, 230–400 mesh, 70/30 hexanes/ethyl acetate) afforded 3-cyclopentyl-N-(4-hydroxymethyl-thiazol-2-yl)-2-(4-phenoxy-phenyl)-propionamide (50 mg, 55%) as a white solid: mp 83.7–87° C.; EI-HRMS m/e calcd for $C_{24}H_{26}N_2O_3S$ (M+) 422.1664, found 422.1674.

EXAMPLE 14

2-[3-Cyclopentyl-2-(4-phenoxy-phenyl)-propionylamino]-thiazole-4-carboxylic acid methyl ester

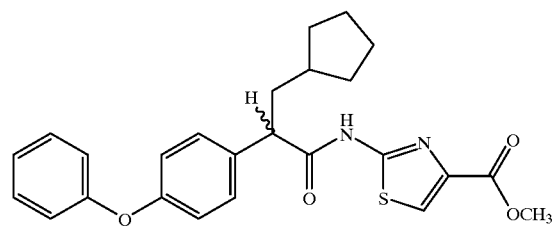

A solution of 2-[3-cyclopentyl-2-(4-phenoxy-phenyl)-propionylamino]-thiazole-4-carboxylic acid ethyl ester (prepared in Example 13, 300 mg, 0.65 mmol) in ethanol (20 mL) at 25° C. was treated with a solution of potassium hydroxide (109 mg, 1.94 mmol) in water (6 mL). This light yellow solution was stirred at 25° C. for 2 h and then concentrated in vacuo to remove ethanol. The resulting aqueous solution was acidified to pH=2 with a 1N aqueous hydrochloric acid solution and then extracted with methylene chloride (3×10 mL). The combined organic extracts were dried over sodium sulfate, filtered, and concentrated in vacuo. Flash chromatography (Merck Silica gel 60, 230–400 mesh, 20/80 hexanes/ethyl acetate plus 1% acetic acid) afforded 2-[3-cyclopentyl-2-(4-phenoxy-phenyl)-propionylamino]-thiazole-4-carboxylic acid (226 mg, 80%) as a white solid: mp >200° C.; FAB-HRMS m/e calcd for $C_{24}H_{24}N_2O_4S$ (M+H)+ 437.1535, found 437.1534.

A solution of 2-[3-cyclopentyl-2-(4-phenoxy-phenyl)-propionylamino]-thiazole-4-carboxylic acid (100 mg, 0.23 mmol) in methanol (10 mL) was treated with concentrated hydrochloric acid (1 mL) and then heated under reflux for 16 h. At this time, the reaction mixture was concentrated in vacuo. The residue was dissolved in ethyl acetate (10 mL) and then washed with water (5 mL). The aqueous layer was further extracted with ethyl acetate (3×5 mL). The combined organic extracts were dried over sodium sulfate, filtered, and concentrated in vacuo. Flash chromatography (Merck Silica gel 60, 230–400 mesh, 90/10 hexanes/ethyl acetate) afforded 2-[3-cyclopentyl-2-(4-phenoxy-phenyl)-propionylamino]-thiazole-4-carboxylic acid methyl ester (40 mg, 39%) as a white foam: EI-HRMS m/e calcd for $C_{25}H_{26}N_2O_4S$ (M+) 450.1613, found 450.1615.

EXAMPLE 15

3-Cyclopentyl-N-[4-(2-hydroxy-ethyl)-thiazol-2-yl]-2-(4-phenoxy-phenyl)-propionamide

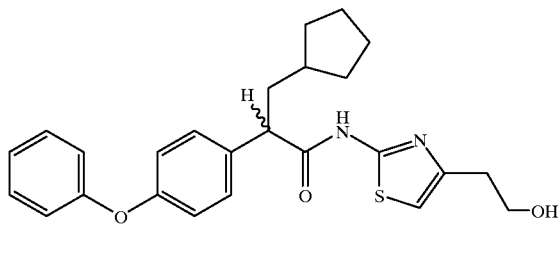

A solution of {2-[3-cyclopentyl-2-(4-phenoxy-phenyl)-propionylamino]-thiazol-4-yl}-acetic acid ethyl ester (prepared in Example 12B-a, 86 mg, 0.18 mmol) in diethyl ether (5 mL) was cooled to 0° C. and then treated with lithium aluminum hydride (10 mg, 0.27 mmol). The reaction mixture was slowly warmed to 25° C. where it was stirred for 16 h. At this time, the reaction mixture was slowly diluted with water (5 mL) and then extracted with ethyl acetate (3×10 mL). The combined organic extracts were dried over sodium sulfate, filtered, and concentrated in vacuo. Flash chromatography (Merck Silica gel 60, 230–400 mesh, 70/30 hexanes/ethyl acetate) afforded 3-cyclopentyl-N-[4-(2-hydroxy-ethyl)-thiazol-2-yl]-2-(4-phenoxy-phenyl)-propionamide (21 mg, 27%) as an off-white solid: FAB-HRMS m/e calcd for $C_{25}H_{28}N_2O_3S$ $(M+H)^+$ 437.1899, found 437.1900.

EXAMPLE 16

{2-[3-Cyclopentyl-2-(4-phenoxy-phenyl)-propionylamino]-thiazol-4-yl}-acetic acid

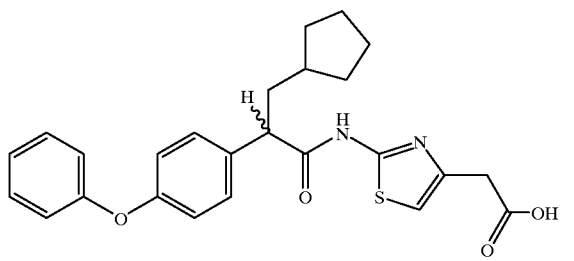

A solution of {2-[3-cyclopentyl-2-(4-phenoxy-phenyl)-propionylamino]-thiazol-4-yl}-acetic acid ethyl ester (prepared in Example 12B-a, 276 mg, 0.58 mmol) in ethanol (20 mL) at 25° C. was treated with a solution of potassium hydroxide (100 mg, 1.78 mmol) in water (6 mL). This light yellow solution was stirred at 25° C. for 2 h and then concentrated in vacuo to remove ethanol. The resulting aqueous solution was acidified to pH=2 with a 1N aqueous hydrochloric acid solution and then extracted with methylene chloride (3×10 mL). The combined organic extracts were dried over sodium sulfate, filtered, and concentrated in vacuo. Flash chromatography (Merck Silica gel 60, 230–400 mesh, 10/90 hexanes/ethyl acetate plus 1% acetic acid) afforded {2-[3-cyclopentyl-2-(4-phenoxy-phenyl)-propionylamino]-thiazol-4-yl}-acetic acid (222 mg, 80%) as a white foam: FAB-HRMS m/e calcd for $C_{25}H_{26}N_2O_4S$ $(M+H)^+$ 451.1691, found 451.1686.

EXAMPLE 17

{2-[3-Cyclopentyl-2-(4-phenoxy-phenyl)-propionylamino]-thiazol-4-yl}-acetic acid methyl ester

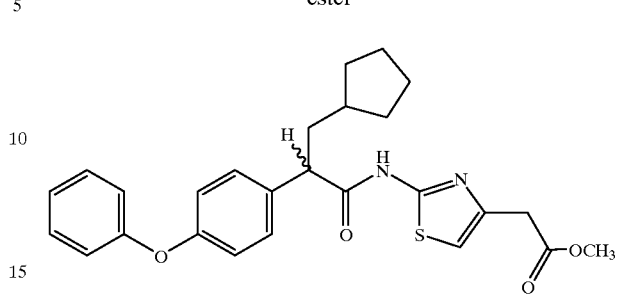

A solution of {2-[3-cyclopentyl-2-(4-phenoxy-phenyl)-propionylamino]-thiazol-4-yl}-acetic acid (prepared in Example 16, 80 mg, 0.18 mmol) in methanol (10 mL) was treated with concentrated hydrochloric acid (1 mL) and then heated under reflux for 16 h. At this time, the reaction mixture was concentrated in vacuo. The residue was dissolved in ethyl acetate (10 mL) and then washed with water (5 mL). The aqueous layer was further extracted with ethyl acetate (3×5 mL). The combined organic extracts were dried over sodium sulfate, filtered, and concentrated in vacuo. Flash chromatography (Merck Silica gel 60, 230–400 mesh, 90/10 hexanes/ethyl acetate) afforded {2-[3-cyclopentyl-2-(4-phenoxy-phenyl)-propionylamino]-thiazol-4-yl}-acetic acid methyl ester (50 mg, 61%) as a yellow oil: EI-HRMS m/e calcd for $C_{26}H_{28}N_2O_4S$ $(M^+)$ 464.1770, found 464.1769.

EXAMPLE 18

3-Cyclopentyl-2-(4-morpholin-4-yl-phenyl)-N-thiazol-2-yl-propionamide

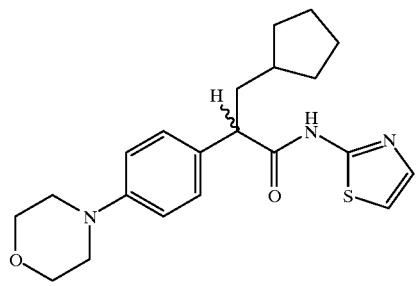

A mixture of 4-morpholinoacetophenone (4.61 g, 22 mmol), sulfur (2.16 g, 67 mmol), and morpholine (6 mL, 67 mmol) was heated at 80° C. for 1 h then heated under reflux for 18 h. The hot reaction mixture was poured into warm ethanol. Upon cooling to 25° C., a precipitate formed. The precipitate was filtered to provide a tan solid (4.16 g). This crude tan solid was then treated with concentrated acetic acid (16 mL), concentrated sulfuric acid (2.4 mL), and water (3.6 mL). The resulting reaction mixture was heated under reflux for 4 h and then poured into water. The water was removed in vacuo to provide crude (4-morpholin-4-yl-phenyl)-acetic acid as a brown oil (8.20 g). This crude (4-morpholin-4-yl-phenyl)-acetic acid was dissolved in methanol (100 mL) and then slowly treated with concentrated sulfuric acid (1 mL). The reaction mixture was heated under reflux for 66 h. The reaction mixture was allowed to cool to 25° C. and then concentrated in vacuo to remove methanol. The residue was diluted with water (200 mL) and then treated with a 10% aqueous sodium hydroxide solution until pH=9. The aqueous phase was extracted with ethyl acetate (3×100 mL). The combined organic extracts were washed with a saturated aqueous sodium chloride solution (1×100 mL), dried over sodium sulfate, filtered, and concentrated in vacuo. Flash chromatography (Merck Silica gel 60, 70–230 mesh, 3/1 to 1/1 hexanes/ethyl acetate gradient elution) afforded (4-morpholin-4-yl-phenyl)-acetic acid methyl ester (2.22 g, 42% for 3 steps) as a yellow oil: EI-HRMS m/e calcd for $C_{13}H_{17}NO_3$ ($M^+$) 235.1208, found 235.1214.

A solution of diisopropylamine (344 μL, 2.45 mmol) in dry tetrahydrofuran (2.9 mL) was cooled to −78° C. under nitrogen and then treated with a 2.5M solution of n-butyllithium in hexanes (981 μL, 2.45 mmol). The reaction mixture was stirred at −78° C. for 15 min and then treated dropwise with a solution of (4-morpholin-4-yl-phenyl)-acetic acid methyl ester (549.9 mg, 2.34 mmol) in dry tetrahydrofuran (2 mL) and 1,3-dimethyl-3,4,5,6-tetrahydro-2(1H)-pyrimidinone (1 mL). The resulting reaction mixture was allowed to stir at −78° C. for 30 min, at which time, a solution of iodomethylcyclopentane (540.0 mg, 2.57 mmol) in a small amount of dry tetrahydrofuran was added dropwise. The reaction mixture was then allowed to warm to 25° C. where it was stirred for 67 h. The reaction mixture was quenched with water and then concentrated in vacuo to remove tetrahydrofuran. The aqueous residue was diluted with ethyl acetate (200 mL). The organic phase was washed with a saturated aqueous sodium chloride solution (1×100 mL), dried over sodium sulfate, filtered, and concentrated in vacuo. Flash chromatography (Merck Silica gel 60, 230–400 mesh, 3/1 hexanes/ethyl acetate) afforded 3-cyclopentyl-2-(4-morpholin-4-yl-phenyl)-propionic acid methyl ester (381.4 mg, 51%) as a white solid: mp 68–70° C.; EI-HRMS m/e calcd for $C_{19}H_{27}NO_3$ ($M^+$) 317.1991, found 317.2001.

A solution of 3-cyclopentyl-2-(4-morpholin-4-yl-phenyl)-propionic acid methyl ester (210.8 mg, 0.66 mmol) in tetrahydrofuran (830 μL) was treated with a 0.8M aqueous lithium hydroxide solution (1.2 mL). The reaction mixture was stirred at 25° C. for 23 h and then concentrated in vacuo to remove tetrahydrofuran. The white residue was acidified to pH=2 with a 10% aqueous hydrochloric solution. The resulting aqueous phase was extracted with ethyl acetate (2×75 mL). The combined organic extracts were washed with a saturated aqueous sodium chloride solution (1×100 mL), dried over sodium sulfate, filtered, and concentrated in vacuo. Trituration from hexanes/diethyl ether afforded 3-cyclopentyl-2-(4-morpholin-4-yl-phenyl)-propionic acid (173.7 mg, 86%) as a white solid: mp 145–147° C.; EI-HRMS m/e calcd for $C_{18}H_{25}NO_3$ ($M^+$) 303.1834, found 303.1843.

A solution of 3-cyclopentyl-2-(4-morpholin-4-yl-phenyl)-propionic acid (202.5 mg, 0.67 mmol) in dry N,N-dimethylformamide (3.3 mL) was treated with N,N-diisopropylethylamine (350 μL, 2.00 mmol), O-benzotriazol-1-yl-N,N,N',N'-tetramethyluronium hexafluorophosphate (303.8 mg, 0.80 mmol), and 2-aminothiazole (133.7 mg, 1.34 mmol). The reaction mixture was stirred at 25° C. under nitrogen for 15 h. The reaction mixture was then concentrated in vacuo to remove N,N-dimethylformamide. The residue was diluted with ethyl acetate (150 mL), and the organic phase was washed with a 10% aqueous hydrochloric acid solution (1×75 mL) and a saturated aqueous sodium chloride solution (1×75 mL). The organic layer was dried over sodium sulfate, filtered, and concentrated in vacuo. Flash chromatography (Merck Silica gel 60, 230–400 mesh, 1/1 hexanes/ethyl acetate) afforded 3-cyclopentyl-2-(4-morpholin-4-yl-phenyl)-N-thiazol-2-yl-propionamide (87.5 mg, 34%) as a white solid: mp 244–246° C.; EI-HRMS m/e calcd for $C_{21}H_{27}N_3O_2S$ ($M^+$) 385.1824, found 385.1832.

EXAMPLE 19

2-(4-Cyclopentanesulfonyl-phenyl)-3-cyclopentyl-N-thiazol-2-yl-propionamide

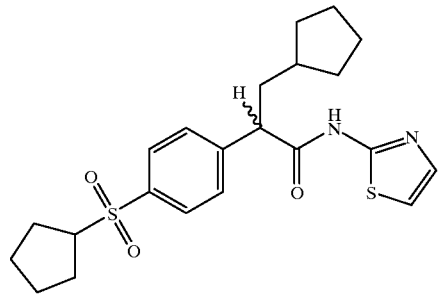

A solution of freshly prepared lithium diisopropylamide (430.55 mL of a 0.3M stock solution, 129.16 mmol) was cooled to −78° C. and then treated with a solution of (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. At this time, the reaction mixture was quenched by the dropwise addition of a saturated aqueous ammonium chloride solution (250 mL). This mixture was concentrated in vacuo, diluted with water (250 mL), and extracted with ethyl acetate (3×300 mL). The combined organic extracts were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ ($M^+$) 291.1470, found 291.1470.

A solution of 3-cyclopentyl-2-(4-nitro-phenyl)-propionic acid ethyl ester (7.37 g, 25.3 mmol) in ethyl acetate (316 mL) was treated with 10% palladium on activated carbon (500 g). The reaction mixture was shaken under 60 psi of hydrogen gas at 25° C. for 18 h. The catalyst was then removed by filtration through a pad of celite and washed with ethyl acetate. The filtrate was concentrated in vacuo to give 2-(4-amino-phenyl)-3-cyclopentyl-propionic acid ethyl ester (3.52 g, 53.3%) as a yellow oil: EI-HRMS m/e calcd for $C_{16}H_{23}NO_2$ ($M^+$) 261.1727, found 261.1727.

A mixture of concentrated hydrochloric acid (0.47 mL) and ice (475 mg) was cooled to 0° C. and then treated with 2-(4-amino-phenyl)-3-cyclopentyl-propionic acid ethyl ester (620 mg, 2.37 mmol). After 5 min, a solution of sodium nitrite (174 mg, 2.51 mmol) in water (0.37 mL) was added to the reaction mixture. The resulting solution was stirred at 0° C. for 5 min. At this time, the solution was added to a solution of cyclopentanethiol (0.29 mL, 2.75 mmol) in water (0.45 mL) warmed to 45° C. The reaction was stirred at 45° C. for 18 h. At this time, the reaction was diluted with water (100 mL) and extracted with chloroform (3×50 mL). The combined organic extracts were dried over sodium sulfate, filtered, and concentrated in vacuo. The crude brown oil (679 mg) was dissolved in methylene chloride (9.80 mL), cooled to 0° C., and then treated with 3-chloroperoxybenzoic acid (80–85% grade, 1.69 g, 9.79 mmol). The reaction mixture was stirred at 25° C. for 18 h. At this time, the reaction was diluted with methylene chloride (100 mL). This solution was washed with a saturated aqueous sodium bisulfite solution (1×100 mL), a saturated aqueous sodium chloride solution (1×100 mL), a saturated aqueous sodium bicarbonate solution (1×100 mL), and a saturated aqueous sodium chloride solution (1×100 mL). The organic layer was dried over sodium sulfate, filtered, and concentrated in vacuo. Flash chromatography (Merck Silica gel 60, 230–400 mesh, 80/20 hexanes/ethyl acetate) afforded 2-(4-cyclopentanesulfonyl-phenyl)-3-cyclopentyl-propionic acid ethyl ester (164 mg, 18.3%) as a red oil: FAB-HRMS m/e calcd for $C_{21}H_{30}O_4S$ $(M+H)^+$ 379.1925 found 379.1943.

A solution of 2-(4-cyclopentanesulfonyl-phenyl)-3-cyclopentyl-propionic acid ethyl ester (160 mg, 0.42 mmol) in tetrahydrofuran/water/methanol (1.05 mL, 3:1:1) was treated with a 1N aqueous lithium hydroxide solution (0.85 mL, 0.85 mmol). The reaction was stirred at 25° C. for 18 h. At this time, the reaction was diluted with chloroform (30 mL) and water (50 mL), acidified to pH=1 with a 1N aqueous hydrochloric acid solution, and extracted with a solution of chloroform/methanol (90/10, 3×50 mL). The combined organic extracts were dried over sodium sulfate, filtered, and concentrated in vacuo. Flash chromatography (Merck Silica gel 60, 230–400 mesh, 90/10 chloroform/methanol) afforded 2-(4-cyclopentanesulfonyl-phenyl)-3-cyclopentyl-propionic acid (101.9 mg, 68.7%) as an off white solid: mp 165–167° C.; FAB-HRMS m/e calcd for $C_{19}H_{26}O_4S$ $(M+H)^+$ 351.1630 found 351.1646.

A solution of triphenylphosphine (106 mg, 0.40 mmol) and N-bromosuccinimide (82 mg, 0.45 mmol) in methylene chloride (1.35 mL) was cooled to 0° C. and then treated with a solution of 2-(4-cyclopentanesulfonyl-phenyl)-3-cyclopentyl-propionic acid (94.8 mg, 0.27 mmol) in methylene chloride. The reaction mixture was stirred at 25° C. for 45 min. At this time, the reaction was treated with 2-aminothiazole (35 mg, 0.35 mmol) and pyridine (0.03 ml, 0.40 mmol). The reaction was stirred at 25° C. for 18 h. The reaction was then diluted with water (100 mL) and extracted with chloroform (3×50 mL). The combined organic extracts were dried over sodium sulfate, filtered, and concentrated in vacuo. Flash chromatography (Merck Silica gel 60, 230–400 mesh, 50/50 hexanes/ethyl acetate) afforded 2-(4-cyclopentanesulfonyl-phenyl)-3-cyclopentyl-N-thiazol-2-yl-propionamide (84 mg, 71.8%) as a light-orange solid: mp 180–182° C.; EI-HRMS m/e calcd for $C_{22}H_{28}N_2O_3S_2$ $(M^+)$ 432.1541 found 432.1543.

In an analogous manner, there were obtained:

From 2-(4-cyclohexanesulfonyl-phenyl)-3-cyclopentyl-propionic acid and 2-aminothiazole: 2-(4-Cyclohexanesulfonyl-phenyl)-3-cyclopentyl-N-thiazol-2-yl-propionamide as an off-white solid: mp 220–222° C.; EI-HRMS m/e calcd for $C_{23}H_{30}N_2O_3S_2$ $(M^+)$ 446.1698 found 446.1700.

From 2-(4-benzenesulfonyl-phenyl)-3-cyclopentyl-propionic acid and 2-aminothiazole: 2-(4-Benzenesulfonyl-phenyl)-3-cyclopentyl-N-thiazol-2-yl-propionamide as a yellow foam: mp 128–131° C.; EI-HRMS m/e calcd for $C_{23}H_{24}N_2O_3S_2$ $(M^+)$ 440.122, found 440.1222.

EXAMPLE 20

3-Cyclopentyl-2-[4-(1H-imidazole-2-sulfonyl)-phenyl]-N-thiazol-2-yl-propionamide

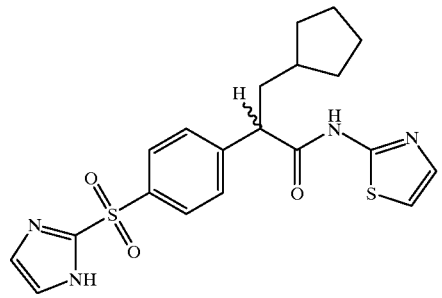

A mixture of concentrated hydrochloric acid (0.49 mL) and ice (493 mg) was cooled to 0° C. and then treated with 2-(4-amino-phenyl)-3-cyclopentyl-propionic acid ethyl ester (prepared in Example 19A, 716 mg, 2.74 mmol). After 5 min, a solution of sodium nitrite (200 mg, 2.90 mmol) in water (0.45 mL) was added to the reaction mixture. The resulting solution was stirred at 0° C. for 5 min. At this time, the solution was added to a solution of 1H-imidazole-2-thiol (318 mg, 1.16 mmol) in water (0.60 mL) warmed to 45° C. The reaction was stirred at 45° C. for 4 h. At this time, the reaction was diluted with water (50 mL) and extracted with chloroform (3×50 mL). The combined organic extracts were dried over sodium sulfate, filtered, and concentrated in vacuo. The crude brown oil (683 mg)was dissolved in formic acid (5.72 mL, 99.71 mmol), cooled to 0° C., and then treated with a 30% aqueous hydrogen peroxide solution (3.82 mL, 9.11 mmol). This solution was stirred at 0° C. for 1 h and at 25° C. for 5 h. At this time, the reaction was quenched by the dropwise addition of a saturated aqueous sodium bisulfite solution. This solution was extracted with chloroform (3×50 mL). The combined organic extracts were washed with a saturated aqueous sodium chloride solution (1×100 mL), dried over sodium sulfate, filtered, and concentrated in vacuo. Flash chromatography (Merck Silica gel 60, 230–400 mesh, 70/30 hexanes/ethyl acetate) afforded 3-cyclopentyl-2-[4-(1H-imidazole-2-sulfonyl)-phenyl]-propionic acid ethyl ester (222.4 mg, 21.5%) as a yellow oil: EI-HRMS m/e calcd for $C_{19}H_{24}N_2O_4S$ $(M^+)$ 376.1456 found 376.1454.

A mixture of 3-cyclopentyl-2-[4-(1H-imidazole-2-sulfonyl)-phenyl]-propionic acid ethyl ester (113.5 mg, 0.30 mmol) and 2-aminothiazole (45.3 mg, 0.45 mmol) in a solution of magnesium methoxide in methanol (7.4 wt. %, 0.86 mL, 0.60 mmol) was heated at 110° C. for 8 h. At this time, the reaction was cooled to 25° C., filtered through a plug of celite, and washed with ethyl acetate. The filtrate was concentrated in vacuo. Flash chromatography (Merck Silica gel 60, 230–400 mesh, 75/25 hexanes/ethyl acetate) afforded the 3-cyclopentyl-2-[4-(1H-imidazole-2-sulfonyl)-phenyl]-N-thiazol-2-yl-propionamide (24.7 mg, 19%) as a tan solid: mp 249–251° C.; EI-HRMS m/e calcd for $C_{20}H_{22}N_4O_2S_2$ $(M^+)$ 430.1133 found 430.1133.

EXAMPLE 21

2-Biphenyl-4-yl-3-cyclopentyl-N-pyridin-2-yl-propionamide

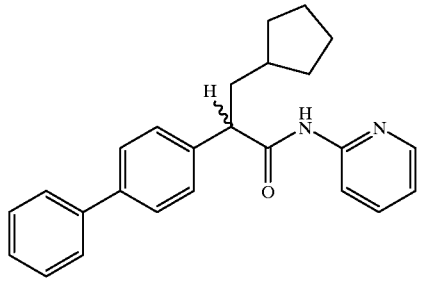

A solution of diisopropylamine (6.93 mL, 49.5 mmol) in dry tetrahydrofuran (64 mL) and 1,3-dimethyl-3,4,5,6-tetrahydro-2(1H)-pyrimidinone (16 mL) was cooled to −78° C. under nitrogen and then treated with a 2.5M solution of n-butyllithium in hexanes (19.8 mL, 49.5 mmol). The yellow reaction mixture was stirred at −78° C. for 30 min and then treated dropwise with a solution of 4-biphenylacetic acid (5.00 g, 23.6 mmol) in a small amount of dry tetrahydrofuran. The reaction mixture turned dark in color and was allowed to stir at −78° C. for 45 min, at which time, a solution of iodomethylcyclopentane (4.96 g, 23.6 mmol) in a small amount of dry tetrahydrofuran was added dropwise. The reaction mixture was allowed to warm to 25° C. over a period of 15 h. The reaction mixture was quenched with water (100 mL), and the reaction mixture was concentrated in vacuo to remove tetrahydrofuran. The remaining aqueous layer was acidified to pH=2 with concentrated hydrochloric acid and then extracted with ethyl acetate (2×150 mL). The combined organic extracts were dried over magnesium sulfate, filtered, and concentrated in vacuo. Flash chromatography (Merck Silica gel 60, 230–400 mesh, 2/1 hexanes/ethyl acetate) afforded 2-biphenyl-4-yl-3-cyclopentylpropionic acid (5.13 g, 74%) as a white solid: mp 131–133° C.; FAB-HRMS m/e calcd for $C_{20}H_{22}O_2$ $(M+H)^+$ 294.1620, found 294.1626.

A solution of 2-biphenyl-4-yl-3-cyclopentylpropionic acid (300 mg, 1.02 mmol), O-benzotriazol-1-yl-N,N,N',N'-tetramethyluronium hexafluorophosphate (386 mg, 1.02 mmol), N,N-diisopropylethylamine (220 µL, 1.22 mmol), and 2-aminopyridine (144 mg, 1.53 mmol) in dry N,N-dimethylformamide (5 ml) was stirred at 25° C. under nitrogen for 15 h. The reaction mixture was partitioned between water and ethyl acetate, and the layers were separated. The organic layer was washed with a 1N aqueous hydrochloric acid solution, water, and a saturated aqueous sodium chloride solution. The organic layer was dried over magnesium sulfate, filtered, and concentrated in vacuo. Flash chromatography (Merck Silica gel 60, 230–400 mesh, 2/1 hexanes/ethyl acetate) afforded 2-biphenyl-4-yl-3-cyclopentyl-N-pyridin-2-yl-propionamide (79 mg, 21%) as a white solid: mp 57–59° C.; EI-HRMS m/e calcd for $C_{25}H_{26}NO$ $(M^+)$ 370.2045, found 370.2049.

EXAMPLE 22

6-(2-Biphenyl-4-yl-3-cyclopentyl-propionylamino)-nicotinic acid methyl ester

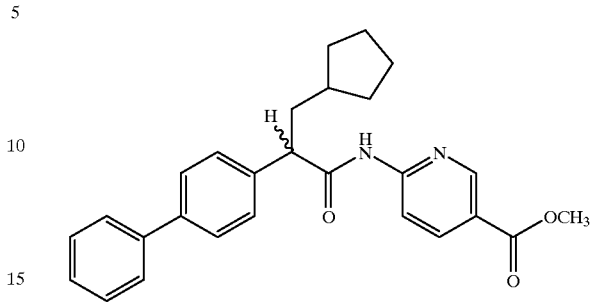

A slurry of 2-biphenyl-4-yl-3-cyclopentylpropionic acid (prepared in Example 21, 1.25 g 4.25 mmol) in methylene chloride (10 mL) was treated with dry N,N-dimethylformamide (5 drops). The reaction mixture was cooled to 0° C. and then treated dropwise with oxalyl chloride (1.85 mL, 21.23 mmol). The reaction mixture was allowed to stir at 0° C. for 30 min and then allowed to warm to 25° C. where it was stirred for 2 h. The reaction mixture was concentrated in vacuo to provide an orange semi-solid residue. This residue was treated with a small amount of methylene chloride and was slowly added to a cooled (0° C.) solution of 6-aminonicotinic acid methyl ester (776 mg, 5.10 mmol) and triethylamine (1.19 mL, 8.50 mmol) in methylene chloride (10 mL). The resulting reaction mixture was stirred at 0° C. and allowed to warm to 25° C. The reaction mixture was stirred at 25° C. for 15 h. The reaction mixture was then concentrated in vacuo to remove methylene chloride. The resulting residue was partitioned between water and ethyl acetate, and the layers were separated. The aqueous layer was further extracted with ethyl acetate (1×100 mL). The combined organic extracts were dried over magnesium sulfate, filtered, and concentrated in vacuo. Flash chromatography (Merck Silica gel 60, 230–400 mesh, 2/1 hexanes/ethyl acetate) afforded 6-(2-biphenyl-4-yl-3-cyclopentyl-propionylamino)-nicotinic acid methyl ester (325 mg, 18%) as a white solid: mp 63–65° C.; EI-HRMS m/e calcd for $C_{27}H_{28}N_2O_3$ $(M^+)$ 428.2099, found 428.2100.

EXAMPLE 23

6-(2-Biphenyl-4-yl-3-cyclopentyl-propionylamino)-nicotinic acid

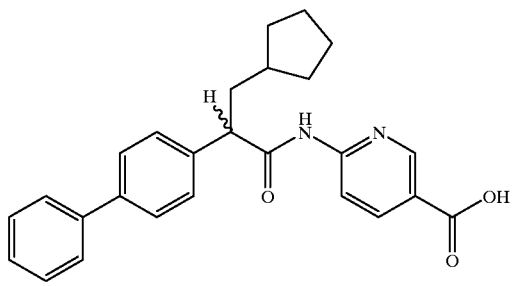

A solution of 6-(2-biphenyl-4-yl-3-cyclopentyl-propionylamino)-nicotinic acid methyl ester (prepared in Example 22, 100 mg, 0.23 mmol) in methanol (2 mL) was treated with a 1N aqueous sodium hydroxide solution (350 mL, 0.35 mmol). The reaction mixture was heated under reflux for 30 min and then allowed to cool to 25° C. The reaction mixture was then concentrated in vacuo. The resulting residue was partitioned between water and ethyl acetate, and the layers were separated. The aqueous layer was further extracted with ethyl acetate (1×25 mL). The combined organic extracts were dried over magnesium sulfate, filtered, and concentrated in vacuo. Flash chromatography (Merck Silica gel 60, 230–400 mesh, 1/1 hexanes/ethyl acetate then 100% methanol) afforded 6-(2-biphenyl-4-yl-3-cyclopentyl-propionylamino)-nicotinic acid (27 mg, 28%) as a white solid: mp 271–272° C. (dec); FAB-HRMS m/e calcd for $C_{26}H_{26}N_2O_3$ $(M+H)^+$ 415.2021, found 415.2010.

EXAMPLE 24

2-Biphenyl-4-yl-3-cyclopentyl-N-(5-hydroxymethyl-pyridin-2-yl)-propionamide

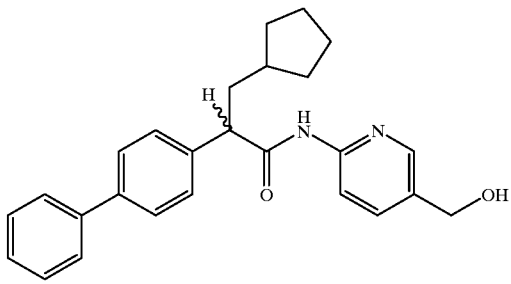

A solution of 6-(2-biphenyl-4-yl-3-cyclopentyl-propionylamino)-nicotinic acid methyl ester (prepared in Example 22, 100 mg, 0.23 mmol) in diethyl ether (3 mL) at 0° C. under nitrogen was slowly treated with lithium aluminum hydride powder (12 mg, 0.30 mmol). The resulting reaction mixture continued to stir at 0° C. and was allowed to gradually warm to 25° C. The reaction mixture was then stirred at 25° C. over a period of 64 h. The reaction mixture was slowly quenched by the dropwise addition of water (5 mL). The resulting reaction mixture was partitioned between water and ethyl acetate, and the layers were separated. The aqueous layer was further extracted with ethyl acetate (1×25 mL). The combined organic extracts were dried over magnesium sulfate, filtered, and concentrated in vacuo. Flash chromatography (Merck Silica gel 60, 230–400 mesh, 1/2 hexanes/ethyl acetate) afforded 2-biphenyl-4-yl-3-cyclopentyl-N-(5-hydroxymethyl-pyridin-2-yl)-propionamide (33 mg, 36%) as a white solid: mp 67–70° C.; EI-HRMS m/e calcd for $C_{26}H_{28}N_2O_2$ $(M^+)$ 400.2151, found 400.2147.

EXAMPLE 25

3-Cyclopentyl-2-(4-naphthalen-1-yl-phenyl)-N-pyridin-2-yl-propionamide

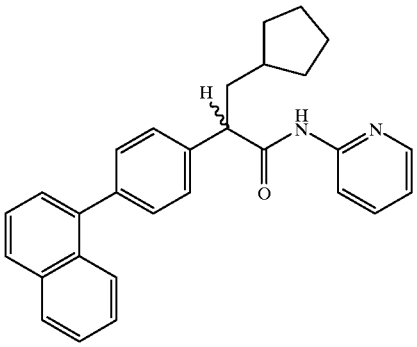

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ $(M^+)$ 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ $(M^+)$ 358.0430, found 358.0434.

A solution of 3-cyclopentyl-2-(4-iodo-phenyl)-propionic acid methyl ester (3.87 g, 10.81 mmol), 1-naphthaleneboronic acid (2.79 g, 16.22 mmol), triethylamine (4.5 mL, 32.44 mmol), palladium (II) acetate (72.8 mg, 0.324 mmol), and tri-o-tolylphosphine (204.1 mg, 0.670 mmol) in dry N,N-dimethylformamide (43 mL) was heated at 100° C. under nitrogen for 1 h. The reaction mixture was allowed to cool to 25° C. and then concentrated in vacuo to remove N,N-dimethylformamide. The residue was diluted with ethyl acetate (200 mL). The organic phase was washed with a saturated aqueous sodium bicarbonate solution (1×100 mL) and water (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-naphthalen-1-yl-phenyl)-propionic acid methyl ester (3.51 g, 90%) as a yellow oil: EI-HRMS m/e calcd for $C_{25}H_{26}O_2$ (M+) 358.1933, found 358.1930.

A solution of 3-cyclopentyl-2-(4-naphthalen-1-yl-phenyl)-propionic acid methyl ester (3.32 g, 9.26 mmol) in tetrahydrofuran (12 mL) was treated with a 0.8M aqueous lithium hydroxide solution (12 mL). The resulting reaction mixture was stirred at 25° C. for 24 h, at which time, thin layer chromatography indicated the presence of starting material. The reaction mixture was then heated at 80° C. for 18 h. The reaction mixture was then allowed to cool to 25° C. and concentrated in vacuo to remove tetrahydrofuran. The residue was acidified to pH=2 with a 10% aqueous hydrochloric acid solution and then extracted with ethyl acetate (2×150 mL). The combined organic extracts were dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-naphthalen-1-yl-phenyl)-propionic acid (1.74 g, 55%) as a white foam: mp 63–64° C.; EI-HRMS m/e calcd for $C_{24}H_{24}O_2$ (M+) 344.1776, found 344.1770.

A solution of 2-aminopyridine (25 mg, 0.26 mmol) in acetonitrile (500 μL) was treated with 3-cyclopentyl-2-(4-naphthalen-1-yl-phenyl)-propionic acid (75 mg, 0.22 mmol), triphenylphosphine (63 mg, 0.24 mmol), triethylamine (91 μL, 0.66 mmol), and carbon tetrachloride (300 μL). The resulting reaction mixture was stirred at 25° C. for 15 h. The cloudy reaction mixture was diluted with water and then extracted with methylene chloride. The organic layer was dried over magnesium sulfate, filtered, and concentrated in vacuo. Flash chromatography (Merck Silica gel 60, 230–400 mesh, 3/1 hexanes/ethyl acetate) afforded impure 3-cyclopentyl-2-(4-naphthalen-1-yl-phenyl)-N-pyridin-2-yl-propionamide. Repurification by flash chromatography (Merck Silica gel 60, 230–400 mesh, 100% methylene chloride) afforded pure 3-cyclopentyl-2-(4-naphthalen-1-yl-phenyl)-N-pyridin-2-yl-propionamide. (40 mg, 43%) as a white foam: mp 73–77° C.; EI-HRMS m/e calcd for $C_{29}H_{28}N_2O$ (M+) 420.2202, found 420.2003.

In an analogous manner, there was obtained:

From 3-cyclopentyl-2-(4-naphthalen-1-yl-phenyl)-propionic acid and 6-aminonicotinic acid methyl ester: 6-[3-Cyclopentyl-2-(4-naphthalen-1-yl-phenyl)-propionylamino]-nicotinic acid methyl ester as a pale yellow foam: mp 78–82° C.; EI-HRMS m/e calcd for $C_{31}H_{30}N_2O_3$ (M+) 478.2256, found 478.2254.

EXAMPLE 26

6-[3-Cyclopentyl-2-(4-naphthalen-1-yl-phenyl)-propionylamino]-nicotinic acid

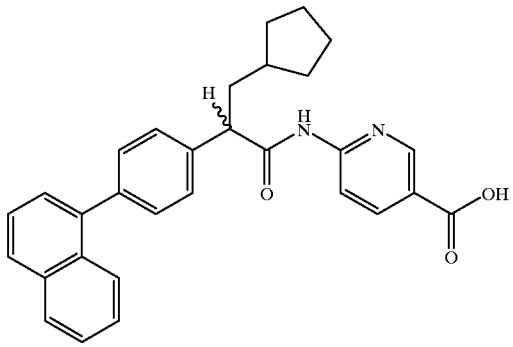

A solution of 6-[3-cyclopentyl-2-(4-naphthalen-1-yl-phenyl)-propionylamino]-nicotinic acid methyl ester (prepared in Example 25B-a, 45 mg, 0.094 mmol) in methanol (500 μL) was treated with a 1N aqueous sodium hydroxide solution (188 μL, 0.188 mmol). The reaction mixture was heated under reflux for 1 h and then allowed to cool to 25° C. The reaction mixture was then concentrated in vacuo. Flash chromatography (Merck Silica gel 60, 230–400 mesh, 15/1 methylene chloride/methanol) afforded 6-[3-cyclopentyl-2-(4-naphthalen-1-yl-phenyl)-propionylamino]-nicotinic acid (15 mg, 34%) as a pale yellow solid: mp 155–158° C.; FAB-HRMS m/e calcd for $C_{30}H_{28}N_2O_3$ (M+H)+ 465.2178, found 465.2169.

EXAMPLE 27

3-Cyclopentyl-N-(5-hydroxymethyl-pyridin-2-yl)-2-(4-naphthalen-1-yl-phenyl)-propionamide

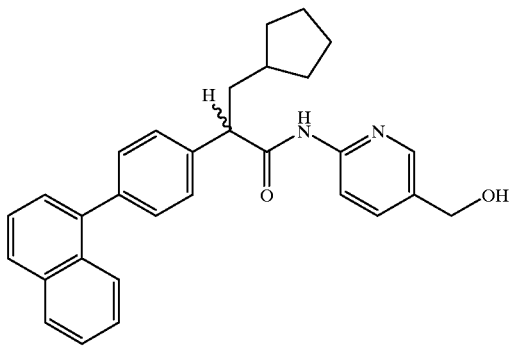

A solution 6-[3-cyclopentyl-2-(4-naphthalen-1-yl-phenyl)-propionylamino]-nicotinic acid methyl ester (prepared in Example 25B-a, 140 mg, 0.29 mmol) in diethyl ether (2 mL) was cooled to 0° C. and then slowly treated with lithium aluminum hydride powder (17 mg, 0.44 mmol). The reaction mixture was stirred at 0° C. for 30 min and then allowed to warm to 25° C. where it was stirred for 3.5 h. The reaction mixture was then slowly quenched by the dropwise addition of water (5 mL). The resulting mixture was partitioned between water (25 mL) and ethyl acetate (25 mL), and the layers were separated. The organic layer was dried over magnesium sulfate, filtered, and concentrated in vacuo. Flash chromatography (Merck Silica gel 60, 230–400 mesh, 1/1 hexanes/ethyl acetate) afforded 3-cyclopentyl-N-(5-hydroxymethyl-pyridin-2-yl)-2-(4-naphthalen-1-yl-phenyl)-propionamide (47 mg, 37%) as a light yellow foam: mp 72–75° C.; EI-HRMS m/e calcd for $C_{30}H_{30}N_2O_2$ ($M^+$) 450.2307, found 450.2312.

EXAMPLE 28

3-Cyclopentyl-N-pyridin-2-yl-2-(4-pyridin-3-yl-phenyl)-propionamide

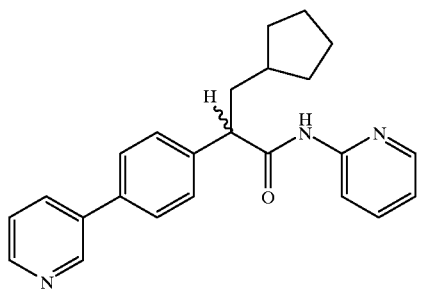

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ ($M^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ ($M^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a solution of pyridine-3-boronic acid (515 mg, 4.19 mmol) and a 2M aqueous sodium carbonate solution (2.8 mL, 5.58 mmol) in water (5 mL). The resulting reaction mixture was heated under reflux for 90 min. The reaction mixture was allowed to cool to 25° C. and then filtered to remove the catalyst. The filtrate was partitioned between water and methylene chloride, and the layers were separated. The aqueous layer was further extracted with methylene chloride (75 mL). The combined organic extracts were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-pyridin-3-yl-phenyl)-propionic acid methyl ester (800 mg, 92%) as a brown oil: EI-HRMS m/e calcd for $C_{20}H_{23}NO_2$ ($M^+$) 309.1729, found 309.1728.

A solution of 3-cyclopentyl-2-(4-pyridin-3-yl-phenyl)-propionic acid methyl ester (450 mg, 1.45 mmol) in tetrahydrofuran (5 mL) was treated with a 0.8M aqueous lithium hydroxide solution (2.18 mL, 1.74 mmol). The resulting reaction mixture was stirred at 25° C. for 3 d. The reaction mixture was then partitioned between water (50 mL) and ethyl acetate (50 mL), and the layers were separated. The aqueous layer was further extracted with ethyl acetate (2×50 mL). The combined organic extracts were dried over magnesium sulfate, filtered, and concentrated in vacuo. The resulting solid was purified by precipitation from methylene chloride/ethyl acetate to afford 3-cyclopentyl-2-(4-pyridin-3-yl-phenyl)-propionic acid (271 mg, 63%) as a white solid: mp 136–138° C.; EI-HRMS m/e calcd for $C_{19}H_{21}NO_2$ ($M^+$) 295.1572, found 295.1572.

A solution of triphenylphosphine (133 mg, 0.51 mmol) in methylene chloride (5 mL) was cooled to 0° C. and then slowly treated with N-bromosuccinimide (90 mg, 0.51 mmol). The reaction mixture was stirred at 0° C. for 20 min and then treated with 3-cyclopentyl-2-(4-pyridin-3-yl-phenyl)-propionic acid (125 mg, 0.42 mmol). The resulting reaction mixture was stirred at 0° C. for 5 min and then allowed to warm to 25° C. where it was stirred for 20 min. The reaction mixture was then treated with 2-aminopyridine (88 mg, 0.93 mmol). The resulting reaction mixture was stirred at 25° C. for 15 h. The crude reaction mixture was then directly purified by flash chromatography (Merck Silica gel 60, 230–400 mesh, 1/2 hexanes/ethyl acetate) to afford impure 3-cyclopentyl-N-pyridin-2-yl-2-(4-pyridin-3-yl-phenyl)-propionamide as a pink foam. The impure foam was dissolved in methylene chloride (40 mL) and washed with a saturated aqueous sodium bicarbonate solution (1×40 mL). The organic layer was dried over magnesium sulfate, filtered and concentrated in vacuo to afford pure 3-cyclopentyl-N-pyridin-2-yl-2-(4-pyridin-3-yl-phenyl)-propionamide (75 mg, 48%) as a pink foam: mp 139–140° C.; EI-HRMS m/e calcd for $C_{24}H_{25}N_3O$ ($M^+$) 371.1998, found 371.2006.

EXAMPLE 29

3-Cyclopentyl-N-pyridin-2-yl-2-(4-pyridin-4-yl-phenyl)-propionamide

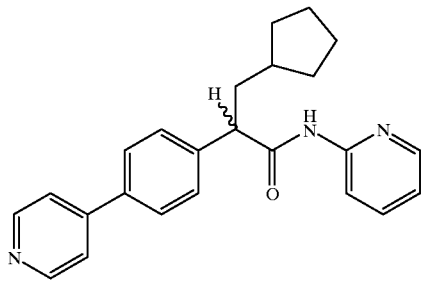

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M$^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M$^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a solution of pyridine-4-boronic acid (515 mg, 4.19 mmol) and a 2M aqueous sodium carbonate solution (2.8 mL, 5.58 mmol) in water (5 mL). The resulting reaction mixture was heated under reflux for 8 h. The reaction mixture was allowed to cool to 25° C. where it was stirred for 3 d. The reaction mixture was partitioned between water (75 mL) and methylene chloride (75 mL), and the layers were separated. The aqueous layer was further extracted with methylene chloride (75 mL). The combined organic extracts were dried over magnesium sulfate, filtered, and concentrated in vacuo to afford 3-cyclopentyl-2-(4-pyridin-4-yl-phenyl)-propionic acid methyl ester (240 mg, 28%) as a brown oil that was used without further purification and characterization.

A solution of 3-cyclopentyl-2-(4-pyridin-4-yl-phenyl)-propionic acid methyl ester (240 mg, 0.78 mmol) in tetrahydrofuran (3 mL) was treated with a 0.8M aqueous lithium hydroxide solution (1.45 mL, 1.16 mmol). The resulting reaction mixture was stirred at 25° C. for 30 min and then heated under reflux for 15 h. The reaction mixture was allowed to cool to 25° C. and then partitioned between water (100 mL) and ethyl acetate (70 mL). The layers were separated, and the aqueous layer was further extracted with ethyl acetate (1×30 mL). The combined organic extracts were dried over magnesium sulfate, filtered, and concentrated in vacuo to afford a yellow oil that solidified upon sitting. The solid was collected to afford 3-cyclopentyl-2-(4-pyridin-4-yl-phenyl)-propionic acid (127 mg, 55%) as a yellow solid: mp 118–121° C.; FAB-HRMS m/e calcd for $C_{19}H_{21}NO_2$ (M+H)$^+$ 296.1650, found 296.1658.

A solution of triphenylphosphine (59 mg, 0.22 mmol) in methylene chloride (1 mL) was cooled to 0° C. and then slowly treated with N-bromosuccinimide (39 mg, 0.22 mmol). The reaction mixture was stirred at 0° C. for 20 min and then treated with 3-cyclopentyl-2-(4-pyridin-4-yl-phenyl)-propionic acid (55 mg, 0.19 mmol). The resulting reaction mixture was stirred at 0° C. for 10 min and then allowed to warm to 25° C., where it was stirred for 20 min. The reaction mixture was then treated with 2-aminopyridine (39 mg, 0.41 mmol). The resulting reaction mixture was stirred at 25° C. for 15 h. The crude reaction mixture was then directly purified by flash chromatography (Merck Silica gel 60, 230–400 mesh, 20/1 methylene chloride/methanol) to afford impure 3-cyclopentyl-N-pyridin-2-yl-2-(4-pyridin-4-yl-phenyl)-propionamide as a yellow solid. Repurification by flash chromatography (Merck Silica gel 60, 230–400 mesh, 100% ethyl acetate) afforded pure 3-cyclopentyl-2-(4-pyridin-4-yl-phenyl)-N-thiazol-2-yl-propionamide (10 mg, 14%) as a yellow solid: mp 165–167° C.; EI-HRMS m/e calcd for $C_{24}H_{25}N_3O$ (M$^+$) 371.1998, found 371.1998.

EXAMPLE 30

3-Cyclopentyl-2-(4-phenoxy-phenyl)-N-pyridin-2-yl-propionamide

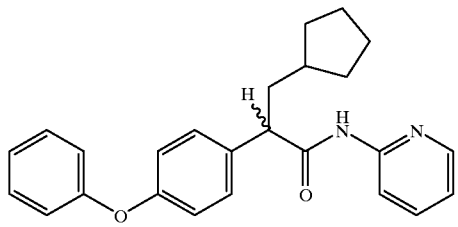

A solution of 3-cyclopentyl-2-(4-phenoxy-phenyl-propionic acid (prepared in Example 12A, 51 mg, 0.16 mmol) in methylene chloride (10 mL) and one drop of N,N-dimethylformamide was cooled to 0° C. and then treated with a 2.0M solution of oxalyl chloride in methylene chloride (0.10 mL, 0.18 mmol). The reaction mixture was stirred at 0° C. for 30 min and then treated with a solution of 2-aminopyridine (32 mg, 0.34 mmol) in tetrahydrofuran (2 mL) and N,N-diisopropylethylamine (0.07 mL, 0.39 mmol). The reaction mixture was stirred at 25° C. for 14 h. At this time, the reaction mixture was diluted with water (10 mL) and then extracted with methylene chloride (3×10 mL). The combined organic extracts were washed with water (1×10 mL), a 1N aqueous sodium hydroxide solution (1×10 mL), and a 1N aqueous hydrochloric acid solution (1×10 mL). The organic layer was dried over sodium sulfate, filtered, and concentrated in vacuo. Flash chromatography (Merck Silica gel 60, 230–400 mesh, 90/10 hexanes/ethyl acetate) afforded 3-cyclopentyl-2-(4-phenoxy-phenyl)-N-pyridin-2-yl-propionamide (22 mg, 35%) as glassy solid: EI-HRMS m/e calcd for $C_{25}H_{26}N_2O_2$ ($M^+$) 386.1994, found 386.2001.

In an analogous manner, there were obtained:

From 3-cyclopentyl-2-(4-phenoxy-phenyl)propionic acid and 2-amino-5-methyl-pyridine: 3-Cyclopentyl-N-(5-methyl-pyridin-2-yl)-2-(4-phenoxy-phenyl)-propionamide as a glassy solid: FAB-HRMS m/e calcd for $C_{26}H_{28}N_2O_2$ $(M+H)^+$ 401.2229, found 401.2229.

From 3-cyclopentyl-2-(4-phenoxy-phenyl)propionic acid and 2-amino-nicotinic acid methyl ester: 6-[3-Cyclopentyl-2-(4-phenoxy-phenyl)-propionylamino]-nicotinic acid methyl ester as a white foam: FAB-HRMS m/e calcd for $C_{27}H_{28}N_2O_4$ $(M+H)^+$ 445.2127, found 445.2127.

EXAMPLE 31

6-[3-Cyclopentyl-2-(4-phenoxy-phenyl)-propionylamino]-nicotinic acid

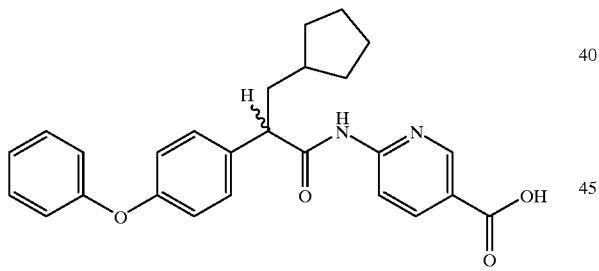

A solution of 6-[3-cyclopentyl-2-(4-phenoxy-phenyl)-propionylamino]-nicotinic acid methyl ester (prepared in Example 30B-b, 102 mg, 0.23 mmol) in ethanol (10 mL) at 25° C. was treated with a solution of potassium hydroxide (40 mg, 0.69 mmol) in water (2.5 mL). This light yellow solution was stirred at 25° C. for 2 h and then concentrated in vacuo to remove ethanol. The resulting aqueous solution was acidified to pH=2 with a 1N aqueous hydrochloric acid solution and then extracted with methylene chloride (3×10 mL). The combined organic extracts were dried over sodium sulfate, filtered, and concentrated in vacuo. Flash chromatography (Merck Silica gel 60, 230–400 mesh, 10/90 hexanes/ethyl acetate plus 1% acetic acid) afforded 6-[3-cyclopentyl-2-(4-phenoxy-phenyl)-propionylamino]-nicotinic acid (74 mg, 76%) as a white solid: FAB-HRMS m/e calcd for $C_{26}H_{26}N_2O_4$ $(M+H)^+$ 431.1971, found 431.1987.

EXAMPLE 32

Cyclopentyl-N-(5-hydroxymethyl-pyridin-2-yl)-2-(4-phenoxy-phenyl)-propionamide

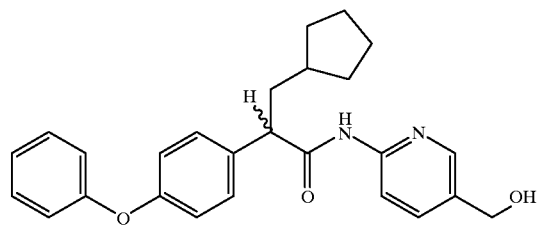

A solution of 6-[3-cyclopentyl-2-(4-phenoxy-phenyl)-propionylamino]-nicotinic acid methyl ester (prepared in Example 30B-b, 59 mg, 0.13 mmol) in diethyl ether (5 mL) was cooled to 0° C. and then treated with lithium aluminum hydride (8 mg, 0.20 mmol). The reaction was slowly warmed to 25° C. where it was stirred for 16 h. At this time, the reaction mixture was slowly diluted with water (5 mL) and then extracted with ethyl acetate (3×10 mL). The combined organic extracts were dried over sodium sulfate, filtered, and concentrated in vacuo. Flash chromatography (Merck Silica gel 60, 230–400 mesh, 50/50 hexanes/ethyl acetate) afforded 3-cyclopentyl-N-(5-hydroxymethyl-pyridin-2-yl)-2-(4-phenoxy-phenyl)-propionamide (28 mg, 51%) as a yellow foam: FAB-HRMS m/e calcd for $C_{26}H_{28}N_2O_3$ $(M+H)^+$ 417.2178, found 417.2163.

EXAMPLE 33

(2-Biphenyl-4-yl-3-cyclopentyl-propionyl) urea

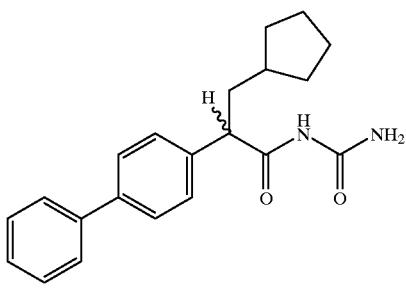

A solution of diisopropylamine (6.93 mL, 49.5 mmol) in dry tetrahydrofuran (64 mL) and 1,3-dimethyl-3,4,5,6-tetrahydro-2(1H)-pyrimidinone (16 mL) was cooled to −78° C. under nitrogen and then treated with a 2.5M solution of n-butyllithium in hexanes (19.8 mL, 49.5 mmol). The yellow reaction mixture was stirred at −78° C. for 30 min and then treated dropwise with a solution of 4-biphenylacetic acid (5.00 g, 23.6 mmol) in a small amount of dry tetrahydrofuran. The reaction mixture turned dark in color and was allowed to stir at −78° C. for 45 min, at which time, a solution of iodomethylcyclopentane (4.96 g, 23.6 mmol) in a small amount of dry tetrahydrofuran was added dropwise. The reaction mixture was allowed to warm to 25° C. over a period of 15 h. The reaction mixture was quenched with water (100 mL), and the reaction mixture was concentrated in vacuo to remove tetrahydrofuran. The remaining aqueous layer was acidified to pH=2 with concentrated hydrochloric acid and then extracted with ethyl acetate (2×150 mL). The combined organic extracts were dried over magnesium sulfate, filtered, and concentrated in vacuo. Flash chromatography (Merck Silica gel 60, 230–400 mesh, 2/1 hexanes/ethyl acetate) afforded 2-biphenyl-4-yl-3-cyclopentylpropionic acid (5.13 g, 74%) as a white solid: mp 131–133° C.; FAB-HRMS m/e calcd for $C_{20}H_{22}O_2$ (M+H)$^+$ 294.1620, found 294.1626.

A solution of 2-biphenyl-4-yl-3-cyclopentylpropionic acid (192.3 mg, 0.653 mmol) in methanol (3.3 mL) was treated slowly with concentrated sulfuric acid (1 drop). The resulting reaction mixture was heated under reflux for 24 h. The reaction mixture was allowed to cool to 25° C. and then concentrated in vacuo to remove methanol. The residue was diluted with ethyl acetate (50 mL). The organic phase was washed with a saturated aqueous sodium bicarbonate solution (1×100 mL), water (1×100 mL), and a saturated aqueous sodium chloride solution (1×100 mL). The organic layer was dried over sodium sulfate, filtered, and concentrated in vacuo. Flash chromatography (Merck Silica gel 60, 70–230 mesh, 9/1 hexanes/ethyl acetate) afforded 2-biphenyl-4-yl-3-cyclopentylpropionic acid methyl ester (191.5 mg, 95%) as a yellow oil: EI-HRMS m/e calcd for $C_{21}H_{24}O_2$ (M$^+$) 308.1776, found 308.1774.

A mixture of 2-biphenyl-4-yl-3-cyclopentylpropionic acid methyl ester (415.5 mg, 1.35 mmol) and urea (202.3 mg, 3.37 mmol, 2.5 equiv) was treated with a solution of magnesium methoxide in methanol (7.4 wt. %, 7.7 mL, 5.39 mmol). The resulting reaction mixture was then heated under reflux for 23 h. The reaction mixture was allowed to cool to 25° C. and then filtered through celite. The filtrate was concentrated in vacuo. Flash chromatography (Merck Silica gel 60, 230–400 mesh, 3/1 hexanes/ethyl acetate then 1/1 hexanes/ethyl acetate) afforded (2-biphenyl-4-yl-3-cyclopentyl-propionyl) urea (67.8 mg, 15%) as a white solid: mp 184–185° C.; FAB-HRMS m/e calcd for $C_{21}H_{24}N_2O_2$ (M+H)$^+$ 337.1917, found 337.1924.

EXAMPLE 34

1-(2-Biphenyl-4-yl-3-cyclopentyl-propionyl)-3-methyl urea

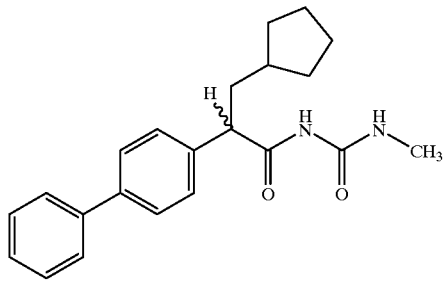

A solution of diisopropylamine (6.93 mL, 49.5 mmol) in dry tetrahydrofuran (64 mL) and 1,3-dimethyl-3,4,5,6-tetrahydro-2(1H)-pyrimidinone (16 mL) was cooled to −78° C. under nitrogen and then treated with a 2.5M solution of n-butyllithium in hexanes (19.8 mL, 49.5 mmol). The yellow reaction mixture was stirred at −78° C. for 30 min and then treated dropwise with a solution of 4-biphenylacetic acid (5.00 g, 23.6 mmol) in a small amount of dry tetrahydrofuran. The reaction mixture turned dark in color and was allowed to stir at −78° C. for 45 min, at which time, a solution of iodomethylcyclopentane (4.96 g, 23.6 mmol) in a small amount of dry tetrahydrofuran was added dropwise. The reaction mixture was allowed to warm to 25° C. over a period of 15 h. The reaction mixture was quenched with water (100 mL), and the reaction mixture was concentrated in vacuo to remove tetrahydrofuran. The remaining aqueous layer was acidified to pH=2 with concentrated hydrochloric acid and then extracted with ethyl acetate (2×150 mL). The combined organic extracts were dried over magnesium sulfate, filtered, and concentrated in vacuo. Flash chromatography (Merck Silica gel 60, 230–400 mesh, 2/1 hexanes/ethyl acetate) afforded 2-biphenyl-4-yl-3-cyclopentylpropionic acid (5.13 g, 74%) as a white solid: mp 131–133° C.; FAB-HRMS m/e calcd for $C_{20}H_{22}O_2$ (M+H)$^+$ 294.1620, found 294.1626.

A solution of 2-biphenyl-4-yl-3-cyclopentylpropionic acid (192.3 mg, 0.653 mmol) in methanol (3.3 mL) was treated slowly with concentrated sulfuric acid (1 drop). The resulting reaction mixture was heated under reflux for 24 h. The reaction mixture was allowed to cool to 25° C. and then concentrated in vacuo to remove methanol. The residue was diluted with ethyl acetate (50 mL). The organic phase was washed with a saturated aqueous sodium bicarbonate solution (1×100 mL), water (1×100 mL), and a saturated aqueous sodium chloride solution (1×100 mL). The organic layer was dried over sodium sulfate, filtered, and concentrated in vacuo. Flash chromatography (Merck Silica gel 60, 70–230 mesh, 9/1 hexanes/ethyl acetate) afforded 2-biphenyl-4-yl-3-cyclopentylpropionic acid methyl ester (191.5 mg, 95%) as a yellow oil: EI-HRMS m/e calcd for $C_{21}H_{24}O_2$ (M$^+$) 308.1776, found 308.1774.

A mixture of 2-biphenyl-4-yl-3-cyclopentylpropionic acid methyl ester (987.4 mg, 3.20 mmol) and methyl urea (948.7 mg, 12.80 mmol) was treated with a solution of magnesium methoxide in methanol (7.4 wt. %, 18 mL, 12.80 mmol). The resulting reaction mixture was then heated under reflux for 19 h. The reaction mixture was allowed to cool to 25° C. and then filtered through celite. The filtrate was concentrated in vacuo. Flash chromatography (Merck Silica gel 60, 230–400 mesh, 3/1 hexanes/ethyl acetate) afforded 1-(2-biphenyl-4-yl-3-cyclopentyl-propionyl)-3-methyl urea (152.5 mg, 14%) as a white solid: mp 195–197° C.; EI-HRMS m/e calcd for $C_{22}H_{26}N_2O_2$ (M$^+$) 350.1994, found 350.2004.

EXAMPLE 35

1-[3-Cyclopentyl-2-(4-naphthalen-1-yl-phenyl)-propionyl]-3-methyl urea

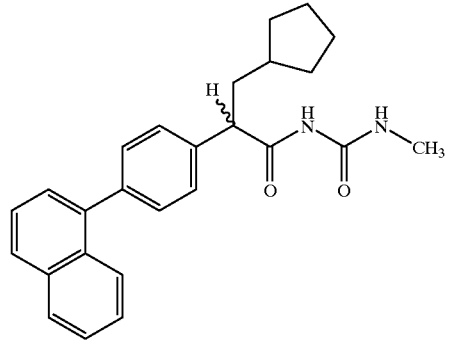

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M+) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M+) 358.0430, found 358.0434.

A solution of 3-cyclopentyl-2-(4-iodo-phenyl)-propionic acid methyl ester (3.87 g, 10.81 mmol), 1-naphthaleneboronic acid (2.79 g, 16.22 mmol), triethylamine (4.5 mL, 32.44 mmol), palladium (II) acetate (72.8 mg, 0.324 mmol), and tri-o-tolylphosphine (204.1 mg, 0.670 mmol) in dry N,N-dimethylformamide (43 mL) was heated at 100° C. under nitrogen for 1 h. The reaction mixture was allowed to cool to 25° C. and then concentrated in vacuo to remove N,N-dimethylformamide. The residue was diluted with ethyl acetate (200 mL). The organic phase was washed with a saturated aqueous sodium bicarbonate solution (1×100 mL) and water (1×100 mL), dried over sodium sulfate, filtered, and concentrated in vacuo. Flash chromatography (Merck Silica gel 60, 70–230 mesh, 19/1 hexanes/ethyl acetate) afforded 3-cyclopentyl-2-(4-naphthalen-1-yl-phenyl)-propionic acid methyl ester (3.51 g, 90%) as a yellow oil: EI-HRMS m/e calcd for $C_{25}H_{26}O_2$ (M+) 358.1933, found 358.1930.

A mixture of 3-cyclopentyl-2-(4-naphthalen-1-yl-phenyl)-propionic acid methyl ester (196.5 mg, 0.548 mmol) and methyl urea (121.8 mg, 1.64 mmol) was treated with a solution of magnesium methoxide in methanol (7.4 wt. %, 3.1 mL, 2.19 mmol). The resulting reaction mixture was then heated under reflux for 24 h. The reaction mixture was allowed to cool to 25° C. and then filtered through celite. The filtrate was concentrated in vacuo. Flash chromatography (Merck Silica gel 60, 230–400 mesh, 9/1 hexanes/ethyl acetate then 3/1 to 1/1 hexanes/ethyl acetate gradient elution) afforded 1-[3-cyclopentyl-2-(4-naphthalen-1-yl-phenyl)-propionyl]-3-methyl urea (76.9 mg, 35%) as a white foam: mp 85–88° C.; EI-HRMS m/e calcd for $C_{26}H_{28}N_2O_2$ (M+) 400.2151, found 400.2150.

EXAMPLE 36

1-[3-Cyclopentyl-2-(4-pyridin-3-yl-phenyl)-propionyl]-3-methyl-urea

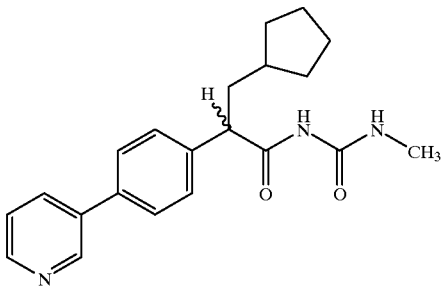

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to −78° C. under nitrogen and then treated with a 10M solution of n-butyllithium in hexanes (12.2 mL, 122.21 mmol). The yellow reaction mixture was stirred at −78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at −78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M+) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M+) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a solution of pyridine-3-boronic acid (515 mg, 4.19 mmol) and a 2M aqueous sodium carbonate solution (2.8 mL, 5.58 mmol) in water (5 mL). The resulting reaction mixture was heated under reflux for 90 min. The reaction mixture was allowed to cool to 25° C. and then filtered to remove the catalyst. The filtrate was partitioned between water and methylene chloride, and the layers were separated. The aqueous layer was further extracted with methylene chloride (75 mL). The combined organic extracts were dried over magnesium sulfate, filtered, and concentrated in vacuo. Flash chromatography (Merck Silica gel 60, 230–400 mesh, 1/1 hexanes/ethyl acetate) afforded 3-cyclopentyl-2-(4-pyridin-3-yl-phenyl)-propionic acid methyl ester (800 mg, 92%) as a brown oil: EI-HRMS m/e calcd for $C_{20}H_{23}NO_2$ (M$^+$) 309.1729, found 309.1728.

A mixture of 3-cyclopentyl-2-(4-pyridin-3-yl-phenyl)-propionic acid methyl ester (275 mg, 0.89 mmol) and methyl urea (165 mg, 2.22 mmol) was treated with a solution of magnesium methoxide in methanol (7.4 wt. %, 5.5 mL, 2.67 mmol). The reaction mixture was then concentrated in vacuo to approximately one-half the volume of methanol. The resulting reaction mixture was then heated under reflux for 3 d. The reaction mixture was allowed to cool to 25° C. and then partitioned between water and ethyl acetate. The layers were separated, and the aqueous layer was further extracted with ethyl acetate (2×40 mL). The combined organic extracts were dried over magnesium sulfate, filtered, and concentrated in vacuo. Flash chromatography (Merck Silica gel 60, 230–400 mesh, 1/3 hexanes/ethyl acetate) afforded 1-[3-cyclopentyl-2-(4-pyridin-3-yl-phenyl)-propionyl]-3-methyl-urea (17 mg, 6%) as a white solid: mp 158–160° C.; FAB-HRMS m/e calcd for $C_{21}H_{25}N_3O_2$ (M+H)$^+$ 352.2025, found 352.2028.

EXAMPLE 37

1-{3-Cyclopentyl-2-[4-(1H-indol-5-yl)-phenyl]-propionyl}-3-methyl-urea

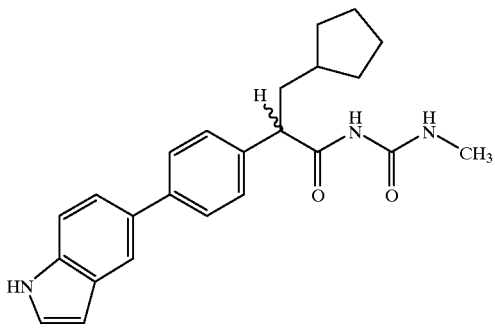

A solution of diisopropylamine (17.1 mL, 122.21 mmol) in dry tetrahydrofuran (55 mL) and 1,3-dimethyl-3,4,5,6-tetrahydro-2(1H)-pyrimidinone (18 mL) was cooled to –78° C. under nitrogen and then treated with a 10M solution of n-butyllithium in hexanes (12.2 mL, 122.21 mmol). The yellow reaction mixture was stirred at –78° C. for 30 min and then treated dropwise with a solution of 4-iodophenylacetic acid (15.25 g, 58.19 mmol) in dry tetrahydrofuran (55 mL) and 1,3-dimethyl-3,4,5,6-tetrahydro-2(1H)-pyrimidinone (18 mL). The reaction mixture turned dark in color and was allowed to stir at –78° C. for 45 min, at which time, a solution of iodomethylcyclopentane (13.45 g, 64.02 mmol) in a small amount of dry tetrahydrofuran was added dropwise. The reaction mixture was allowed to warm to 25° C. where it was stirred for 42 h. The reaction mixture was concentrated in vacuo to remove tetrahydrofuran and then quenched with a 10% aqueous hydrochloric acid solution (100 mL). The resulting aqueous layer was extracted with ethyl acetate (3×200 mL). The combined organic extracts were washed with a saturated aqueous sodium chloride solution (1×200 mL), dried over sodium sulfate, filtered, and concentrated in vacuo. Flash chromatography (Merck Silica gel 60, 70–230 mesh, 3/1 hexanes/ethyl acetate) afforded 3-cyclopentyl-2-(4-iodo-phenyl)-propionic acid (13.97 g, 70%) as a cream solid: mp 121–122° C.; EI-HRMS m/e calcd for $C_{14}H_{17}IO_2$ (M$^+$) 344.0273, found 344.0275.

A solution of 3-cyclopentyl-2-(4-iodo-phenyl)-propionic acid (13.00 g, 37.77 mmol) in methanol (94 mL) was treated slowly with concentrated sulfuric acid (5 drops). The resulting reaction mixture was heated under reflux for 67 h. The reaction mixture was allowed to cool to 25° C. and then concentrated in vacuo to remove methanol. The residue was diluted with ethyl acetate (300 mL). The organic phase was washed with a saturated aqueous sodium chloride solution (1×100 mL), dried over sodium sulfate, filtered, and concentrated in vacuo. Flash chromatography (Merck Silica gel 60, 70–230 mesh, 100% hexanes then 19/1 hexanes/ethyl acetate) afforded 3-cyclopentyl-2-(4-iodo-phenyl)-propionic acid methyl ester (13.18 g, 97%) as a yellow semi-solid: EI-HRMS m/e calcd for $C_{15}H_{19}IO_2$ (M$^+$) 358.0430, found 358.0434.

A slurry of dichlorobis(triphenylphosphine)palladium(II) (119 mg, 0.17 mmol) in 1,2-dimethoxyethane (10 mL) was treated with 3-cyclopentyl-2-(4-iodo-phenyl)-propionic acid methyl ester (1.00 g, 2.79 mmol). The reaction slurry was stirred at 25° C. for 10 min and then treated with a mixture of 5-indolylboronic acid (670 mg, 4.19 mmol) in water (5 mL) and a 2M aqueous sodium carbonate solution (2.8 mL, 5.58 mmol). The resulting reaction mixture was heated under reflux for 2 h. The reaction mixture was allowed to cool to 25° C. and then filtered to remove the catalyst. The filtrate was partitioned between water (50 mL) and methylene chloride (50 mL), and the layers were separated. The aqueous layer was further extracted with methylene chloride (50 mL). The combined organic extracts were dried over magnesium sulfate, filtered, and concentrated in vacuo. Flash chromatography (Merck Silica gel 60, 230–400 mesh, 1/2 hexanes/ethyl acetate) afforded 3-cyclopentyl-2-[4-(1H-indol-5-yl)-phenyl]-propionic acid methyl ester (347 mg, 36%) as a light brown oil: EI-HRMS m/e calcd for $C_{23}H_{25}NO_2$ (M$^+$) 347.1885, found 347.1887.

A mixture of 3-cyclopentyl-2-[4-(1H-indol-5-yl)-phenyl]-propionic acid methyl ester (245 mg, 0.71 mmol) and methyl urea (131 mg, 1.76 mmol) was treated with a solution of magnesium methoxide in methanol (7.4 wt. %, 5.5 mL, 2.12 mmol). The reaction mixture was then concentrated in vacuo to approximately one-half the volume of methanol. The resulting reaction mixture was then heated under reflux for 15 h. The reaction mixture was allowed to cool to 25° C. and then partitioned between water (20 mL) and ethyl acetate (50 mL). The layers were separated, and the aqueous layer was further extracted with ethyl acetate (1×25 mL). The combined organic extracts were dried over magnesium sulfate, filtered, and concentrated in vacuo. Flash chromatography (Merck Silica gel 60, 230–400 mesh, 1/1 hexanes/ethyl acetate) afforded 1-{3-cyclopentyl-2-[4-(1H-indol-5-yl)-phenyl]-propionyl}-3-methyl-urea (79 mg, 29%) as a white foam: mp 91–95° C. (foam to gel); FAB-HRMS m/e calcd for $C_{24}H_{27}N_3O_2$ (M+H)$^+$ 390.2181, found 390.2192.

EXAMPLE 38

1-[3-Cyclopentyl-2-(4-phenoxy-phenyl)-propionyl]-3-methyl-urea

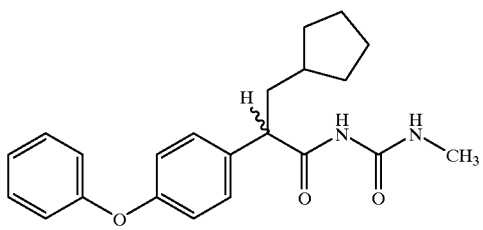

A solution of diisopropylamine (2.52 mL, 19.3 mmol) in tetrahydrofuran (50 mL) was cooled to −78° C. under a nitrogen atmosphere and then treated with a 2.5M solution of n-butyllithium in hexanes (7.7 mL, 19.3 mmol). The reaction mixture was stirred at −78° C. for 15 min and then slowly treated with a solution of 4-phenoxyphenylacetic acid (2.00 g, 8.8 mmol) in tetrahydrofuran (12 mL) and 1,3-dimethyl-3,4,5,6-tetrahydro-2(1H)-pyrimidinone (4 mL) via cannulation. The resulting bright yellow solution was allowed to stir for 1 h at −78° C. After this time, the reaction mixture was treated with a solution of iodomethylcyclopentane (2.02 g, 9.6 mmol) in 1,3-dimethyl-3,4,5,6-tetrahydro-2(1H)-pyrimidinone (1 mL) via cannulation. The resulting reaction mixture was stirred for 1 h at −78° C. and then allowed to warm to 25° C. where it was stirred for 14 h. The reaction was then acidified to pH=2 by the dropwise addition of a 1N aqueous hydrochloric acid solution and then extracted with ethyl acetate (3×25 mL). The combined organic extracts were dried over sodium sulfate, filtered and concentrated in vacuo. Flash chromatography (Merck Silica gel 60, 230–400 mesh, 50/50 hexanes/ethyl acetate plus 1% acetic acid) afforded 3-cyclopentyl-2-(4-phenoxy-phenyl) propionic acid (2.49 g, 91%) as a white foam: EI-HRMS m/e calcd for $C_{20}H_{22}O_3$ (M$^+$) 310.1568, found 310.1568.

A solution of 3-cylopentyl-2-(4-phenoxy-phenyl)-propionic acid (200 mg, 0.64 mmol) in methylene chloride (10 mL) with one drop of N,N-dimethylformamide was cooled to 0° C. under a nitrogen atmosphere. The reaction mixture was then treated with a 2.0M solution of oxalyl chloride in methylene chloride (0.48 mL, 0.97 mmol), and the resulting reaction mixture was stirred at 0° C. for 30 min. The reaction mixture was then treated with 1,1,1,3,3,3-hexamethyldisilazane (0.47 mL, 2.24 mmol) and then allowed to warm to 25° C. where it was stirred for 16 h. After such time, the reaction mixture was treated with methanol (10 mL) and then allowed to stir at 25° C. for 10 min. The resulting reaction mixture was washed with a 5% aqueous sulfuric acid solution (2×10 mL). The combined aqueous extracts were further extracted with methylene chloride (2×10 mL). The combined organic extracts were then washed with a saturated aqueous sodium chloride solution (1×10 mL), dried over magnesium sulfate, filtered, and concentrated in vacuo. Flash chromatography (Merck Silica gel 60, 230–400 mesh, 50/50 hexanes/ethyl acetate) afforded 3-cyclopentyl-2-(4-phenoxy-phenyl)-propionamide (120 mg, 61%,) as a white solid: mp 91.6–94.4° C.; EI-HRMS m/e calcd for $C_{20}H_{23}NO_2$ (M$^+$) 309.1729, found 309.1733.

A solution of 3-cyclopentyl-2-(4-phenoxy-phenyl)-propionamide (143 mg, 0.46 mmol) in toluene (10 mL) was treated with methyl isocyanate (0.04 mL, 0.69 mmol). The reaction mixture was heated under reflux for 24 h. The reaction was then concentrated in vacuo. Flash chromatography (Merck Silica gel 60, 230–400 mesh, 80/20 hexanes/ethyl acetate) afforded 1-[3-cyclopentyl-2-(4-phenoxy-phenyl)-propionyl]-3-methyl-urea (116 mg, 69%) as a white solid: EI-HRMS m/e calcd for $C_{22}H_{26}N_2O_3$ (M$^+$) 366.1943, found 366.1946.

EXAMPLE 39

1-[3-Cyclopentyl-2-(4-morpholin-4-yl-phenyl)-propionyl]-3-methyl-urea

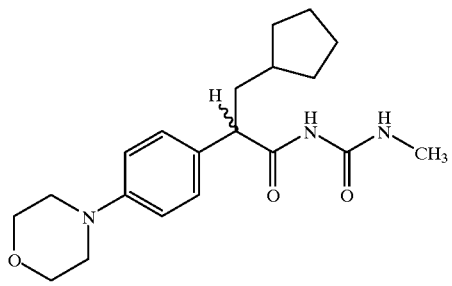

A mixture of 4-morpholinoacetophenone (4.61 g, 22 mmol), sulfur (2.16 g, 67 mmol), and morpholine (6 mL, 67 mmol) was heated at 80° C. for 1h then heated under reflux for 18 h. The hot reaction mixture was poured into warm ethanol. Upon cooling to 25° C., a precipitate formed. The precipitate was filtered to provide a tan solid (4.16 g). This crude tan solid was then treated with concentrated acetic acid (16 mL), concentrated sulfuric acid (2.4 mL), and water (3.6 mL). The resulting reaction mixture was heated under reflux for 4 h and then poured into water. The water was removed in vacuo to provide crude (4-morpholin-4-yl-phenyl)-acetic acid as a brown oil (8.20 g). This crude (4-morpholin-4-yl-phenyl)-acetic acid was dissolved in methanol (100 mL) and then slowly treated with concentrated sulfuric acid (1 mL). The reaction mixture was heated under reflux for 66 h. The reaction mixture was allowed to cool to 25° C. and then concentrated in vacuo to remove methanol. The residue was diluted with water (200 mL) and then treated with a 10% aqueous sodium hydroxide solution until pH=9. The aqueous phase was extracted with ethyl acetate (3×100 mL). The combined organic extracts were washed with a saturated aqueous sodium chloride solution (1×100 mL), dried over sodium sulfate, filtered, and concentrated in vacuo. Flash chromatography (Merck Silica gel 60, 70–230 mesh, 3/1 to 1/1 hexanes/ethyl acetate gradient elution) afforded (4-morpholin-4-yl-phenyl)-acetic acid methyl ester (2.22 g, 42% for 3 steps) as a yellow oil: EI-HRMS m/e calcd for $C_{13}H_{17}NO_3$ (M$^+$) 235.1208, found 235.1214.

A solution of diisopropylamine (344 μL, 2.45 mmol) in dry tetrahydrofuran (2.9 mL) was cooled to −78° C. under nitrogen and then treated with a 2.5M solution of n-butyllithium in hexanes (981 μL, 2.45 mmol). The reaction mixture was stirred at −78° C. for 15 min and then treated dropwise with a solution of (4-morpholin-4-yl-phenyl)-acetic acid methyl ester (549.9 mg, 2.34 mmol) in dry tetrahydrofuran (2 mL) and 1,3-dimethyl-3,4,5,6-tetrahydro-2(1H)-pyrimidinone (1 mL). The resulting reaction mixture was allowed to stir at −78° C. for 30 min, at which time, a solution of iodomethylcyclopentane (540.0 mg, 2.57 mmol) in a small amount of dry tetrahydrofuran was added dropwise. The reaction mixture was then allowed to warm to 25° C. where it was stirred for 67 h. The reaction mixture was quenched with water and then concentrated in vacuo to remove tetrahydrofuran. The aqueous residue was diluted with ethyl acetate (200 mL). The organic phase was washed with a saturated aqueous sodium chloride solution (1×100 mL), dried over sodium sulfate, filtered, and concentrated in vacuo. Flash chromatography (Merck Silica gel 60, 230–400 mesh, 3/1 hexanes/ethyl acetate) afforded 3-cyclopentyl-2-(4-morpholin-4-yl-phenyl)-propionic acid methyl ester (381.4 mg, 51%) as a white solid: mp 68–70° C.; EI-HRMS m/e calcd for $C_{19}H_{27}NO_3$ (M$^+$) 317.1991, found 317.2001.

A mixture of 3-cyclopentyl-2-(4-morpholin-4-yl-phenyl)-propionic acid methyl ester (364.0 mg, 1.15 mmol) and methyl urea (254.8 mg, 3.44 mmol) was treated with a solution of magnesium methoxide in methanol (7.4 wt. %, 6.6 mL, 4.59 mmol). The resulting reaction mixture was heated under reflux for 3 d. The reaction mixture was allowed to cool to 25° C. and then filtered through a pad of celite. The pad of celite was washed well with ethyl acetate until the washings showed the absence of product by thin layer chromatography. The filtrate was then concentrated in vacuo. Flash chromatography (Merck Silica gel 60, 230–400 mesh, 3/1 hexanes/ethyl acetate then 1/1 hexanes/ethyl acetate) afforded 1-[3-cyclopentyl-2-(4-morpholin-4-yl-phenyl)-propionyl]-3-methyl-urea (43.5 mg, 11%) as a white solid: mp 206–207° C.; FAB-HRMS m/e calcd for $C_{20}H_{29}N_3O_3$ (M$^+$) 359.2209, found 359.2206.

EXAMPLE 40

1-[2-(4-Cyclohexanesulfonyl-phenyl)-3-cyclopentyl-propionyl]-3-methyl-urea

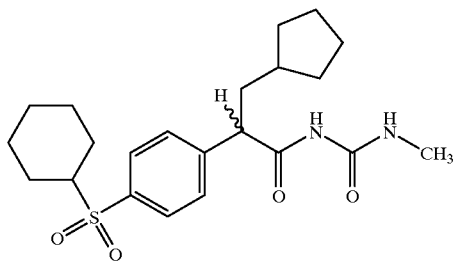

A solution of freshly prepared lithium diisopropylamide (430.55 mL of a 0.3M stock solution, 129.16 mmol) was cooled to −78° C. and then treated with a solution of (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. The reaction mixture was then quenched by the dropwise addition of a saturated aqueous ammonium chloride solution (250 mL). This mixture was concentrated in vacuo, diluted with water (250 mL), and extracted with ethyl acetate (3×300 mL). The combined organic extracts were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ (M$^+$) 291.1470, found 291.1470.

A solution of 3-cyclopentyl-2-(4-nitro-phenyl)-propionic acid ethyl ester (7.37 g, 25.3 mmol) in ethyl acetate (316 mL) was treated with 10% palladium on activated carbon (500 g). The reaction mixture was shaken under 60 psi of hydrogen gas at 25° C. for 18 h. The catalyst was then filtered off through a pad of celite and was washed with ethyl acetate. The filtrate was concentrated in vacuo to give 2-(4-amino-phenyl)-3-cyclopentyl-propionic acid ethyl ester (3.52 g, 53.3%) as a yellow oil: EI-HRMS m/e calcd for $C_{16}H_{23}NO_2$ (M$^+$) 261.1727, found 261.1727.

A mixture of concentrated hydrochloric acid (0.32 mL) and ice (320 mg) was cooled to 0° C. and then treated with 2-(4-amino-phenyl)-3-cyclopentyl-propionic acid ethyl ester (419.4 mg, 1.60 mmol). After 5 min, a solution of sodium nitrite (117 mg, 1.70 mmol) in water (0.26 mL) was added to the reaction mixture. The resulting solution was stirred at 0° C. for 5 min. At this time, the solution was added to a solution of cyclohexanethiol (0.23 mL, 1.86 mmol) in water (0.35 mL) warmed to 45° C. The reaction was stirred at 45° C. for 12 h. At this time, the reaction was diluted with water (100 mL) and extracted with ethyl acetate (3×50 mL). The combined organic extracts were dried over sodium sulfate, filtered, and concentrated in vacuo. The residue was passed through a plug of silica (90/10 hexanes/ethyl acetate) to afford a crude brown oil (128.2 mg). This oil was dissolved in methylene chloride (8.8 mL), cooled to 0° C., and then treated with 3-chloroperoxybenzoic acid (80–85% grade, 307 mg, 1.77 mmol). The reaction mixture was stirred at 25° C. for 1.5 h. At this time, the reaction was diluted with ethyl acetate (50 mL). This solution was washed with a saturated aqueous sodium bisulfite solution (1×50 mL) and a saturated aqueous sodium chloride solution (1×50 mL). The organic layer was dried over sodium sulfate, filtered, and concentrated in vacuo. Flash chromatography (Merck Silica gel 60, 230–400 mesh, 80/20 hexanes/ethyl acetate) afforded 2-(4-cyclohexanesulfonyl-phenyl)-3-cyclopentyl-propionic acid ethyl ester (37.7 mg, 23.7%) as a brown oil: EI-HRMS m/e calcd for $C_{22}H_{32}O_4S$ (M$^+$) 392.2021 found 392.2022.

A mixture of 2-(4-cyclohexanesulfonyl-phenyl)-3-cyclopentyl-propionic acid ethyl ester (71.5 mg, 0.16 mmol) and methyl urea (18 mg, 0.24 mmol) was treated with a solution of magnesium methoxide in methanol (7.4 wt. %, 0.46 mL, 0.32 mmol). The resulting reaction mixture was heated at 100° C. for 8 h. At this time, the reaction was cooled to 25° C. and passed through a plug of celite. The celite was washed with ethyl acetate. The filtrate was concentrated in vacuo. Flash chromatography (Merck Silica gel 60, 230–400 mesh, 50/50 hexanes/ethyl acetate) afforded 1-[3-cyclopentyl-2-(3,4-difluoro-phenyl)-propionyl]-3-methyl-urea (12.6 mg, 18.7%) as a white solid: mp 244–246° C.; FAB-HRMS m/e calcd for $C_{16}H_{20}F_2N_2O_2$ (M+H)$^+$ 421.2153, found 421.2161.

BIOLOGICAL ACTIVITY EXAMPLES

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2). Recombinant Scheme 2

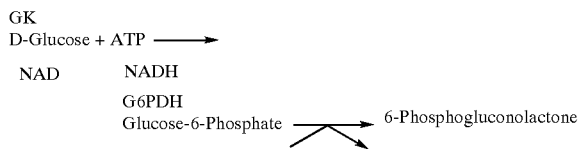

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 µl. The incubation mixture contained: 25 mM Hepes buffer (pH, 7.1), 25 mM KCl, 5 mM D-glucose, 1 mM ATP, 1.8 mM NAD, 2 mM MgCl$_2$, 1 µM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in OD$_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the SC$_{1.5}$, was calculated. All of the compounds of formula I described in the Synthesis Examples had an SC$_{1.5}$ less than or equal to 30 µM.

What is claimed is:
1. An amide selected from the group consisting of a compound of the formula

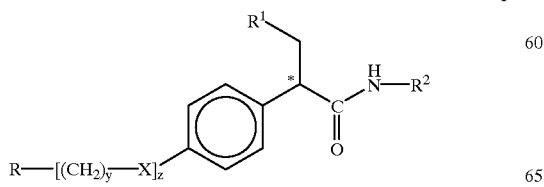

I wherein X is —O— or

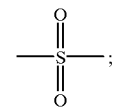

wherein

R is a heteroaromatic ring, connected by a ring carbon atom, which contains from 5 to 6 ring members with from 1 to 2 heteroatoms selected from the group consisting of oxygen, sulfur or nitrogen, aryl containing 6 or 10 ring carbon atoms, aryl containing from 6 to 10 ring carbon atoms fused with a heteroaromatic ring containing 5 or 6 ring members with 1 or 2 heteroatoms in the ring being selected from the group consisting of nitrogen, oxygen or sulfur, or a saturated 5- or 6-membered cycloheteroalkyl ring, which contains from 1 to 2 heteroatoms selected from the group consisting of oxygen, sulfur and nitrogen, or a cycloalkyl ring having 5 or 6 carbon atoms;

R$^1$ is a cycloalkyl ring having 5 or 6 carbon atoms; R$^2$ is

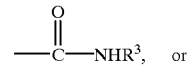

a five- or six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen which is adjacent to the connecting ring carbon atom, said heteroaromatic ring being unsubstituted or monosubstituted at a position on a ring carbon atom other than adjacent to said connecting carbon atom with a substituent selected from the group consisting of lower alkyl, —(CH$_2$)$_n$—OR$^6$,

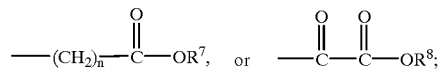

n is 0, 1, 2, 3 or 4; y and z are independently 0 or 1, * denotes the asymmetric carbon atom center; R$^3$ is hydrogen, lower alkyl or

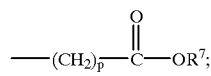

R$^6$, R$^7$ and R$^8$ are independently hydrogen or lower alkyl; and p is an integer from 0 to 5; or a pharmaceutically acceptable salt thereof.

2. The amide of claim 1 wherein said compound is

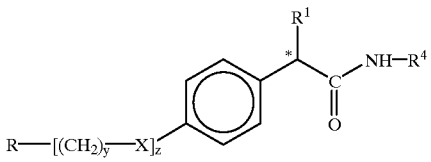

I-B wherein

*, y, z, X, R and $R^1$ are as above, $R^4$ is a five- or six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen which is adjacent to the connecting ring carbon atom, said heteroaromatic ring being unsubstituted or monosubstituted at a position on a ring carbon atom other than adjacent to said connecting carbon atom with a substituent selected from the group consisting of lower alkyl, —$(CH_2)_n$—$OR^6$,

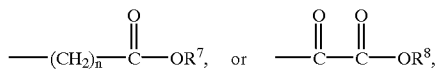

n is 0, 1, 2, 3 or 4;

and $R^6$, $R^7$ and $R^8$ are independently hydrogen or lower alkyl.

3. The amide of claim 2 wherein z is 0.

4. The amide of claim 3 wherein $R^1$ is cyclopentyl.

5. The amide of claim 4 wherein R is aryl.

6. The amide of claim 5 wherein $R^4$ is a substituted or unsubstituted five-membered heteroaromatic ring.

7. The amide of claim 6 wherein said heteroaromatic ring defined by $R^4$ is an unsubstituted thiazolyl.

8. The amide of claim 7 wherein said compound is 2-biphenyl-4-yl-3-cyclopentyl-N-thiazol-2-yl-propionamide.

9. The amide of claim 8 wherein said compound is (2R)-2-biphenyl-4-yl-3-cyclopentyl-N-thiazol-2-yl-propionamide.

10. The amide of claim 6 wherein said compound is 3-cyclopentyl-2-(4-naphthalen-1-yl-phenyl)-N-thiazol-2-yl-propionamide.

11. The amide of claim 6 wherein $R^4$ is thiazolyl which is substituted with

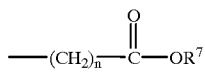

and $R^7$ is as above.

12. The amide of claim 11 wherein said compound is [2-(2-biphenyl-4-yl-3-cyclopentyl-propionylamino)-thiazol-4-yl]-acetic acid methyl ester.

13. The amide of claim 11 wherein said compound is [2-(2-biphenyl-4-yl-3-cyclopentyl-propionylamino)-thiazol-4-yl]-acetic acid ethyl ester.

14. The amide of claim 11 wherein said compound is 2-(2-biphenyl-4-yl-3-cyclopentyl-propionylamino)-thiazole-4-carboxylic acid ethyl ester.

15. The amide of claim 11 wherein said compound is 2-(2-biphenyl-4-yl-3-cyclopentyl-propionylamino)-thiazole-4-carboxylic acid methyl ester.

16. The amide of claim 11 wherein said compound is {2-[3-cyclopentyl-2-(4-naphthalen-1-yl-phenyl)-propionylamino]-thiazol-4-yl}-acetic acid methyl ester.

17. The amide of claim 11 wherein said compound is {2-[3-cyclopentyl-2-(4-naphthalen-1-yl-phenyl)-propionylamino]-thiazol-4-yl}-acetic acid ethyl ester.

18. The amide of claim 11 wherein said compound is 2-[3-cyclopentyl-2-(4-naphthalen-1-yl-phenyl)-propionylamino]-thiazole-4-carboxylic acid methyl ester.

19. The amide of claim 6 wherein $R^2$ is thiazolyl substituted with —$(CH_2)_n$—$OR^6$ or

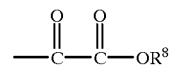

and n, $R^6$ and $R^8$ are as above.

20. The amide of claim 19 wherein said compound is [2-(2-biphenyl-4-yl-3-cyclopentyl-propionylamino)-thiazol-4-yl]-oxo-acetic acid ethyl ester.

21. The amide of claim 19 wherein said compound is 2-biphenyl-4-yl-3-cyclopentyl-N-(4-hydroxymethyl-thiazol-2-yl)-propionamide.

22. The amide of claim 19 wherein said compound is 2-biphenyl-4-yl-3-cyclopentyl-N-[4-(2-hydroxyethyl)-thiazol-2-yl]-propionamide.

23. The amide of claim 19 wherein said compound is 3-cyclopentyl-N-[4-(2-hydroxyethyl)-thiazol-2-yl]-2-(4-naphthalen-1-yl-phenyl)-propionamide.

24. The amide of claim 19 wherein said compound is 3-cyclopentyl-N-(4-hydroxymethyl-thiazol-2-yl)-2-(4-naphthalen-1-yl-phenyl)-propionamide.

25. The amide of claim 5 wherein $R^4$ is unsubstituted pyridinyl.

26. The amide of claim 25 wherein said compound is 2-biphenyl-4-yl-3-cyclopentyl-N-pyridin-2-yl-propionamide.

27. The amide of claim 25 wherein said compound is 3-cyclopentyl-2-(4-naphthalen-1-yl-phenyl)-N-pyridin-2-yl-propionamide.

28. The amide of claim 5 wherein said compound is pyridine monosubstituted with a —$(CH_2)_n$—$OR^6$ or

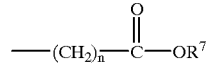

groups.

29. The compound of claim 28 wherein said compound is 6-(2-biphenyl-4-yl-3-cyclopentyl-propionylamino)-nicotinic acid methyl ester.

30. The compound of claim 28 wherein said compound is 6-(2-biphenyl-4-yl-3-cyclopentyl-propionylamino)-nicotinic acid.

31. The compound of claim 28 wherein said compound is 2-biphenyl-4-yl-3-cyclopentyl-N-(5-hydroxymethyl-pyridin-2-yl)-propionamide.

32. The compound of claim 28 wherein said compound is 6-[3-cyclopentyl-2-(4-naphthalen-1-yl-phenyl)-propionylamino]-nicotinic acid methyl ester.

33. The compound of claim 28 wherein said compound is 6-[3-cyclopentyl-2-(4-naphthalen-1-yl-phenyl)-propionylamino]-nicotinic acid.

34. The compound of claim 28 wherein said compound is 3-cyclopentyl-N-(5-hydroxymethyl-pyridin-2-yl)-2-(4-naphthalen-1-yl-phenyl)-propionamide.

35. The compound of claim 4 wherein R is a heteroaromatic ring containing from 5 to 6 ring members with from 1 to 2 heteroatoms selected form the group consisting of oxygen, sulfur or nitrogen in the ring.

36. The compound of claim 35 wherein $R^4$ selected from the group consisting of unsubstituted or monosubstituted pyridinyl or thiazolyl.

37. The compound of claim 36 wherein said compound is 3-cyclopentyl-N-thiazol-2-yl-2-(4-thiophen-2-yl-phenyl)-propionamide.

38. The compound of claim 36 wherein said compound is 3-cyclopentyl-2-(4-pyridin-3-yl-phenyl)-N-thiazol -2-yl-propionamide.

39. The compound of claim 36 wherein said compound is 3-cyclopentyl-2-(4-pyridin-4-yl-phenyl)-N-thiazol-2-yl-propionamide.

40. The amide of claim 36 wherein said compound is 3-cyclopentyl-N-pyridin-2-yl-2-(4-pyridin-4-yl-phenyl)-propionamide.

41. The amide of claim 36 wherein said compound is 3-cyclopentyl-N-pyridin-2-yl-2-(4-pyridin-3-yl-phenyl)-propionamide.

42. The amide of claim 4 wherein R is aryl fused to a heteroaromatic ring containing from 5 to 6 ring members with from 1 to 2 heteroatoms in the ring selected from the group consisting of oxygen, nitrogen or sulfur.

43. The amide of claim 42 wherein said compound $R^4$ is thiazolyl.

44. The amide of claim 43 wherein said compound is 3-cyclopentyl-2-[4-(1H-indol-5-yl)-phenyl]-N-thiazol-2-yl-propionamide.

45. The amide of claim 4 wherein R is a saturated 5- or 6-membered cycloheteroalkyl.

46. The amide of claim 45 wherein $R^4$ is thiazole.

47. The amide of claim 46 wherein said amide is 3-cyclopentyl-2-(4-morpholin-4-yl-phenyl)-N-thiazol-2-yl-propionamide.

48. The amide of claim 2 wherein said compound is the formula

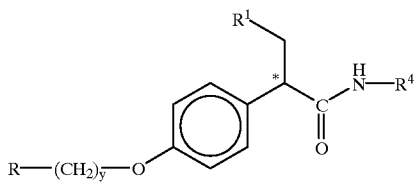

wherein R, $R^1$, $R^2$ and y are as above.

49. The amide of claim 48 wherein R is aryl.

50. The amide of claim 49 wherein $R^4$ is unsubstituted pyridinyl or thiazolyl.

51. The amide of claim 50 wherein said compound is 2-(4-benzyloxy-phenyl)-3-cyclopentyl-N-thiazol-2-yl-propionamide.

52. The amide of claim 50 wherein said compound is 3-cyclopentyl-2-(4-phenoxy-phenyl)-N-thiazol-2-yl-propionamide.

53. The amide of claim 50 wherein said compound is 3-cyclopentyl-2-(4-phenoxy-phenyl)-N-pyridin-2-yl-propionamide.

54. The amide of claim 49 wherein $R^4$ is substituted thiazolyl.

55. The amide of claim 54 wherein said compound is {2-[3-cyclopentyl-2-(4-phenoxy-phenyl)-propionylamino]-thiazol-4-yl}-acetic acid ethyl ester.

56. The amide of claim 54 wherein said compound is 3-cyclopentyl-N-(4-hydroxymethyl-thiazol-2-yl)-2-(4-phenoxy-phenyl)-propionamide.

57. The amide of claim 54 wherein said compound is 2-[3-cyclopentyl-2-(4-phenoxy-phenyl)-propionylamino]-thiazole-4-carboxylic acid methyl ester.

58. The amide of claim 54 wherein said compound is 3-cyclopentyl-N-[4-(2-hydroxy-ethyl)-thiazol-2-yl]-2-(4-phenoxy-phenyl)-propionamide.

59. The amide of claim 54 wherein said compound is {2-[3-cyclopentyl-2-(4-phenoxy-phenyl)-propionylamino]-thiazol-4-yl }-acetic acid.

60. The amide of claim 54 wherein said compound is {2-[3-cyclopentyl-2-(4-phenoxy-phenyl)-propionylamino]-thiazol-4-yl}-acetic acid methyl ester.

61. The amide of claim 49 wherein $R^4$ is substituted pyridinyl.

62. The amide of claim 61 wherein said compound is 3-cyclopentyl-N-(5-methyl-pyridin-2-yl)-2-(4-phenoxy-phenyl)-propionamide.

63. The amide of claim 61 wherein said compound is 6-[3-cyclopentyl-2-(4-phenoxy-phenyl)-propionylamino]-nicotinic acid methylester.

64. The amide of claim 61 wherein said compound is 6-[3-cyclopentyl-2-(4-phenoxy-phenyl)-propionylamino]-nicotinic acid.

65. The amide of claim 61 wherein said compound is 3-cyclopentyl-N-(5-hydroxymethyl-pyridin-2-yl)-2-(4-phenoxy-phenyl)-propionamide.

66. The amide of claim 2 wherein said compound has the formula

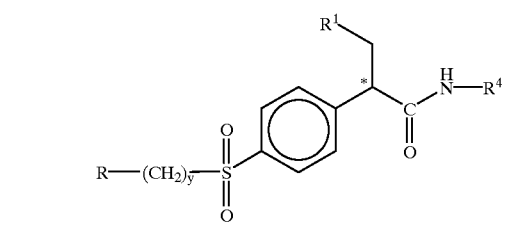

wherein y, R, $R^1$ and $R^4$ are as above.

67. The amide of claim 66 wherein $R^1$ is cyclopentyl.

68. The amide of claim 67 wherein $R^4$ is unsubstituted or monosubstituted thiazolyl.

69. The amide of claim 68 wherein R is aryl.

70. The amide of claim 69 wherein said compound is 2-(4-benzenesulfonyl-phenyl)-3-cyclopentyl-N-thiazol-2-yl-propionamide.

71. The amide of claim 68 wherein R is cycloalkyl.

72. The amide of claim 71 wherein said compound is 2-(4-cyclopentanesulfonyl-phenyl)-3-cyclopentyl-N-thiazol-2-yl-propionamide.

73. The amide of claim 71 wherein said compound is 2-(4-cyclohexanesulfonyl-phenyl)-3-cyclopentyl-N-thiazol-2-yl-propionamide.

74. The amide of claim 68 wherein R is a heteroaromatic ring.

75. The amide of claim 74 wherein said compound is 3-cyclopentyl-2-[4-(1H-imidazole-2-sulfonyl)-phenyl]-N-thiazol-2-yl-propionamide.

76. The amide of claim 1 being the formula:

wherein y, z, X, R, $R^1$ and $R^3$ are as above.

77. The amide of claim 76 wherein $R^1$ is cyclopentyl.

78. The amide of claim 77 wherein z is 0.

79. The amide of claim 78 wherein R is aryl.

80. The amide of claim 79 wherein said compound is (2-biphenyl-4-yl-3-cyclopentyl-propionyl)-urea.

81. The amide of claim 79 wherein said compound is 1-(2-biphenyl-4-yl-3-cyclopentyl-propionyl)-3-methyl-urea.

82. The amide of claim 79 wherein said compound is 1-[3-cyclopentyl-2-(4-naphthalen-1-yl-phenyl)-propionyl]-3-methyl-urea.

83. The amide of claim 78 wherein R is a heteroaromatic ring containing from 5 to 6 ring members with from 1 to 3 heteroatoms selected from the group consisting of oxygen, sulfur or nitrogen.

84. The amide of claim 83 wherein said compound is 1-[3-cyclopentyl-2-(4-pyridin-3-yl-phenyl)-propionyl]-3-methyl-urea.

85. The amide of claim 78 wherein R is aryl fused with a heteroaromatic containing from 5 to 6 ring members.

86. The amide of claim 85 wherein said compound is 1-{3-cyclopentyl-2-[4-(1H-indol-5-yl)-phenyl]-propionyl}-3-methyl-urea.

87. The amide of claim 78 wherein R is a saturated 5- or 6-membered cycloheteroalkyl ring containing from 1 to 2 heteroatoms selected from the group consisting of oxygen, nitrogen and sulfur.

88. The amide of claim 87 wherein said compound is 1-[3-cyclopentyl-2-(4-morpholin-4-yl-phenyl)-propionyl]-3-methyl-urea.

89. The amide of claim 77 wherein y is 0 and z is 1.

90. The amide of claim 89 wherein R is a saturated cycloalkyl ring.

91. The amide of claim 90 wherein X is $SO_2$.

92. The amide of claim 91 wherein said compound is 1-[2-(4-cyclohexanesulfonyl-phenyl)-3-cyclopentyl-propionyl]-3-methyl-urea.

93. The amide of claim 90 wherein X is oxygen.

94. The amide of claim 93 wherein R is aryl.

95. The amide of claim 94 wherein said compound is 1-[3-cyclopentyl-2-(4-phenoxy-phenyl)-propionyl]-3-methyl-urea.

* * * * *

UNITED STATES PATENT AND TRADEMARK OFFICE
CERTIFICATE OF CORRECTION

PATENT NO. : 6,384,220 B2
DATED : May 7, 2002
INVENTOR(S) : Wendy Lea Corbett et al.

It is certified that error appears in the above-identified patent and that said Letters Patent is hereby corrected as shown below:

Title page,
Item [75], Inventor, replace "Cedar Grove" with -- Pine Brook --.

Column 67,
Lines 3-10, replace present formula with
--
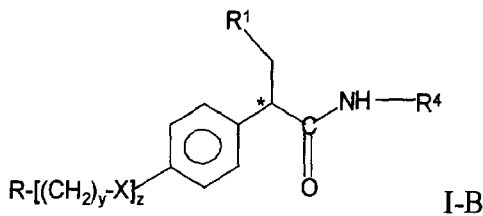
I-B
--.

Column 69,
Line 3, replace "form" with -- from --.
Line 5, after "$R^{4"}$" insert -- is --.

Signed and Sealed this

Seventh Day of January, 2003

JAMES E. ROGAN
*Director of the United States Patent and Trademark Office*